US012642584B2

(12) United States Patent
Beeckler et al.

(10) Patent No.: US 12,642,584 B2
(45) Date of Patent: Jun. 2, 2026

(54) IRRIGATED BALLOON CATHETER WITH FLEXIBLE CIRCUIT ELECTRODE ASSEMBLY

(71) Applicant: BIOSENSE WEBSTER (ISRAEL) LTD., Yokneam (IL)

(72) Inventors: Christopher Thomas Beeckler, Brea, CA (US); Joseph Thomas Keyes, Sierra Madre, CA (US); Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 1352 days.

(21) Appl. No.: 16/866,314

(22) Filed: May 4, 2020

(65) Prior Publication Data

US 2020/0261152 A1 Aug. 20, 2020

Related U.S. Application Data

(63) Continuation of application No. 15/360,964, filed on Nov. 23, 2016, now Pat. No. 10,653,480, and a
(Continued)

(51) Int. Cl.
*A61B 18/14* (2006.01)
*A61B 5/00* (2006.01)
(Continued)

(52) U.S. Cl.
CPC .......... *A61B 18/1492* (2013.01); *A61B 5/283* (2021.01); *A61B 5/287* (2021.01);
(Continued)

(58) Field of Classification Search
CPC .............. A61B 18/1492; A61B 5/6853; A61B 2018/0016; A61B 2018/0022; A61B 2018/1405; A61B 2562/164
See application file for complete search history.

(56) References Cited

U.S. PATENT DOCUMENTS

D123,782 S 12/1940 Lux
3,316,896 A 5/1967 Thomasset
(Continued)

FOREIGN PATENT DOCUMENTS

CN 1225027 A 8/1999
CN 101422637 A 5/2009
(Continued)

OTHER PUBLICATIONS

YouTube, "Intensity™ CX4 Professional E-Stim/Ultrasound Combo", Dec. 22, 2015, Retrieved from internet [https://www.youtube.com/watch?v=76s1QKMWJME], retrieved on Nov. 19, 2020, 1 page.
(Continued)

*Primary Examiner* — Jaymi E Della
(74) *Attorney, Agent, or Firm* — Calderon Safran & Wright P.C.; Etan S. Chatlynne

(57) ABSTRACT

A method of constructing an electrophysiology catheter having a flex circuit electrode assembly includes: providing a flex circuit having a substrate, a first conductive layer and a second conductive layer; removing the first conductive layer to expose a first surface of the substrate; forming the wiring electrode in the second conductive layer with one exclusion zone; forming a first through-hole in the substrate to provide one conductive via and forming a second through-hole to provide an irrigation aperture in alignment with the exclusion zone; forming the contact electrode on first surface of the substrate; placing conductive material into the first through-hole to form the conductive via, the conductive via extending through the substrate and electrically coupling the wiring electrode and the contact electrode; and coupling a first conductor and a second conductor to the wiring electrode to form a thermocouple.

29 Claims, 18 Drawing Sheets

Related U.S. Application Data continuation of application No. 15/360,966, filed on Nov. 23, 2016, now Pat. No. 10,660,700, which is a continuation-in-part of application No. 15/172,118, filed on Jun. 2, 2016, now abandoned, said application No. 15/360,964 is a continuation-in-part of application No. 15/172,118, filed on Jun. 2, 2016, now abandoned, said application No. 15/360,966 is a continuation-in-part of application No. 15/141,751, filed on Apr. 28, 2016, now Pat. No. 10,638,976, said application No. 15/360,964 is a continuation-in-part of application No. 15/141,751, filed on Apr. 28, 2016, now Pat. No. 10,638,976.

(51) Int. Cl.

| | |
|---|---|
| *A61B 5/283* | (2021.01) |
| *A61B 5/287* | (2021.01) |
| *G03F 7/16* | (2006.01) |
| *H05K 3/40* | (2006.01) |
| *H05K 3/46* | (2006.01) |
| *A61B 17/00* | (2006.01) |
| *A61B 18/00* | (2006.01) |

(52) U.S. Cl.
CPC .......... *A61B 5/6853* (2013.01); *A61B 5/6857* (2013.01); *G03F 7/16* (2013.01); *H05K 3/4038* (2013.01); *H05K 3/4644* (2013.01); *A61B 2017/00526* (2013.01); *A61B 2018/00029* (2013.01); *A61B 2018/00083* (2013.01); *A61B 2018/0016* (2013.01); *A61B 2018/0022* (2013.01); *A61B 2018/00375* (2013.01); *A61B 2018/00577* (2013.01); *A61B 2018/00642* (2013.01); *A61B 2018/00702* (2013.01); *A61B 2018/00791* (2013.01); *A61B 2018/00821* (2013.01); *A61B 2018/00839* (2013.01); *A61B 2018/00892* (2013.01); *A61B 2018/1405* (2013.01); *A61B 2018/1465* (2013.01); *A61B 2018/1497* (2013.01); *A61B 2218/002* (2013.01); *A61B 2562/125* (2013.01); *A61B 2562/164* (2013.01)

(56) References Cited

U.S. PATENT DOCUMENTS

| | | | |
|---|---|---|---|
| 4,232,676 A * | 11/1980 | Herczog | A61B 18/14 |
| | | | 606/50 |
| 4,276,874 A | 7/1981 | Wolvek et al. | |
| 4,587,975 A | 5/1986 | Salo et al. | |
| 4,709,698 A | 12/1987 | Johnston et al. | |
| 4,805,621 A | 2/1989 | Heinze et al. | |
| 5,085,636 A | 2/1992 | Burns | |
| 5,178,957 A | 1/1993 | Kolpe et al. | |
| 5,391,199 A | 2/1995 | Ben-Haim | |
| 5,429,617 A | 7/1995 | Hammersmark et al. | |
| 5,582,609 A | 12/1996 | Swanson et al. | |
| 5,584,830 A | 12/1996 | Ladd et al. | |
| 5,702,386 A | 12/1997 | Stern et al. | |
| 5,718,241 A | 2/1998 | Ben-Haim et al. | |
| 5,797,903 A | 8/1998 | Swanson et al. | |
| 5,860,974 A | 1/1999 | Abele | |
| 5,971,983 A | 10/1999 | Lesh | |
| 6,012,457 A | 1/2000 | Lesh | |
| 6,024,740 A | 2/2000 | Lesh et al. | |
| 6,042,580 A | 3/2000 | Simpson | |
| 6,091,993 A | 7/2000 | Bouchier et al. | |
| 6,123,718 A | 9/2000 | Tu et al. | |
| 6,142,993 A | 11/2000 | Whayne et al. | |
| 6,164,283 A | 12/2000 | Lesh | |
| 6,171,275 B1 | 1/2001 | Webster, Jr. | |
| 6,176,832 B1 | 1/2001 | Habu et al. | |
| 6,198,974 B1 | 3/2001 | Webster, Jr. | |
| 6,226,542 B1 | 5/2001 | Reisfeld | |
| 6,239,724 B1 | 5/2001 | Doron et al. | |
| 6,301,496 B1 | 10/2001 | Reisfeld | |
| 6,322,558 B1 | 11/2001 | Taylor et al. | |
| 6,322,559 B1 | 11/2001 | Daulton et al. | |
| 6,325,777 B1 | 12/2001 | Zadno-Azizi et al. | |
| 6,332,089 B1 | 12/2001 | Acker et al. | |
| 6,380,957 B1 | 4/2002 | Banning | |
| 6,402,740 B1 | 6/2002 | Ellis et al. | |
| D462,389 S | 9/2002 | Provence et al. | |
| 6,471,693 B1 | 10/2002 | Carroll et al. | |
| 6,484,118 B1 | 11/2002 | Govari | |
| 6,522,930 B1 * | 2/2003 | Schaer | A61B 18/1492 |
| | | | 607/104 |
| 6,618,612 B1 | 9/2003 | Acker et al. | |
| 6,656,174 B1 | 12/2003 | Hegde et al. | |
| 6,690,963 B2 | 2/2004 | Ben-Haim et al. | |
| 6,771,996 B2 | 8/2004 | Bowe et al. | |
| 6,814,733 B2 | 11/2004 | Schwartz et al. | |
| 6,892,091 B1 | 5/2005 | Ben-Haim et al. | |
| 6,893,433 B2 | 5/2005 | Lentz | |
| 6,986,744 B1 | 1/2006 | Krivitski | |
| 6,987,995 B2 | 1/2006 | Drysen | |
| 6,997,924 B2 | 2/2006 | Schwartz et al. | |
| 7,066,895 B2 | 6/2006 | Podany | |
| 7,142,903 B2 | 11/2006 | Rodriguez et al. | |
| 7,156,816 B2 | 1/2007 | Schwartz et al. | |
| 7,274,957 B2 | 9/2007 | Drysen | |
| 7,340,307 B2 | 3/2008 | Maguire et al. | |
| 7,377,906 B2 | 5/2008 | Selkee | |
| 7,442,190 B2 | 10/2008 | Abboud et al. | |
| 7,536,218 B2 | 5/2009 | Govari et al. | |
| 7,591,799 B2 | 9/2009 | Selkee | |
| 7,593,760 B2 | 9/2009 | Rodriguez et al. | |
| 7,720,517 B2 | 5/2010 | Drysen | |
| 7,756,576 B2 | 7/2010 | Levin | |
| 7,842,031 B2 | 11/2010 | Abboud et al. | |
| 7,853,302 B2 | 12/2010 | Rodriguez et al. | |
| 8,000,765 B2 | 8/2011 | Rodriguez et al. | |
| 8,021,327 B2 | 9/2011 | Selkee | |
| 8,048,032 B2 | 11/2011 | Root et al. | |
| 8,231,617 B2 | 7/2012 | Satake | |
| 8,267,932 B2 | 9/2012 | Baxter et al. | |
| 8,275,440 B2 | 9/2012 | Rodriguez et al. | |
| 8,348,888 B2 | 1/2013 | Selkee | |
| 8,357,152 B2 | 1/2013 | Govari et al. | |
| D682,289 S | 5/2013 | Dijulio et al. | |
| D682,291 S | 5/2013 | Baek et al. | |
| D690,318 S | 9/2013 | Kluttz et al. | |
| D694,652 S | 12/2013 | Tompkin | |
| 8,641,709 B2 | 2/2014 | Sauvageau et al. | |
| 8,721,590 B2 | 5/2014 | Seward et al. | |
| 8,777,161 B2 | 7/2014 | Pollock et al. | |
| D716,340 S | 10/2014 | Bresin et al. | |
| 8,852,181 B2 | 10/2014 | Malecki et al. | |
| D720,766 S | 1/2015 | Mandal et al. | |
| D721,379 S | 1/2015 | Moon et al. | |
| D724,618 S | 3/2015 | Shin | |
| 8,974,450 B2 * | 3/2015 | Brannan | A61B 18/1815 |
| | | | 606/41 |
| 8,998,893 B2 | 4/2015 | Avitall | |
| D729,263 S | 5/2015 | Ahn et al. | |
| 9,089,350 B2 | 7/2015 | Willard | |
| D736,780 S | 8/2015 | Wang | |
| 9,126,023 B1 | 9/2015 | Sahatjian et al. | |
| D740,308 S | 10/2015 | Kim et al. | |
| D743,424 S | 11/2015 | Danielyan et al. | |
| D744,000 S | 11/2015 | Villamor et al. | |
| 9,173,758 B2 | 11/2015 | Brister et al. | |
| D747,742 S | 1/2016 | Fan et al. | |
| D750,644 S | 3/2016 | Bhutani et al. | |
| 9,283,034 B2 | 3/2016 | Katoh et al. | |
| 9,289,141 B2 | 3/2016 | Lowery et al. | |
| D753,690 S | 4/2016 | Vazquez et al. | |
| 9,320,631 B2 | 4/2016 | Moore et al. | |
| 9,345,540 B2 | 5/2016 | Mallin et al. | |
| D759,673 S | 6/2016 | Looney et al. | |
| D759,675 S | 6/2016 | Looney et al. | |

(56)　　　　　References Cited

U.S. PATENT DOCUMENTS

| | | | |
|---|---|---|---|
| D764,500 S | 8/2016 | Wang | |
| D765,709 S | 9/2016 | Gagnier | |
| D767,616 S | 9/2016 | Jones et al. | |
| D768,696 S | 10/2016 | Gagnier | |
| D783,037 S | 4/2017 | Hariharan et al. | |
| 9,655,677 B2 | 5/2017 | Salahieh et al. | |
| D791,805 S | 7/2017 | Segars | |
| 9,795,442 B2 | 10/2017 | Salahieh et al. | |
| 9,907,610 B2 | 3/2018 | Beeckler et al. | |
| 9,956,035 B2 | 5/2018 | Govari et al. | |
| D861,717 S | 10/2019 | Brekke et al. | |
| 10,668,258 B1 | 6/2020 | Calhoun et al. | |
| 10,688,278 B2 | 6/2020 | Beeckler et al. | |
| 2001/0031961 A1 | 10/2001 | Hooven | |
| 2002/0002369 A1 | 1/2002 | Hood | |
| 2002/0065455 A1 | 5/2002 | Ben-Haim et al. | |
| 2002/0068931 A1 | 6/2002 | Wong et al. | |
| 2002/0077627 A1 | 6/2002 | Johnson et al. | |
| 2002/0160134 A1 | 10/2002 | Ogushi et al. | |
| 2003/0018327 A1 | 1/2003 | Truckai et al. | |
| 2003/0028183 A1 | 2/2003 | Sanchez et al. | |
| 2003/0050637 A1 | 3/2003 | Maguire et al. | |
| 2003/0060820 A1 | 3/2003 | Maguire et al. | |
| 2003/0120150 A1 | 6/2003 | Govari | |
| 2003/0144658 A1 | 7/2003 | Schwartz et al. | |
| 2003/0178032 A1 | 9/2003 | Ingle et al. | |
| 2004/0068178 A1 | 4/2004 | Govari | |
| 2004/0122445 A1 | 6/2004 | Butler et al. | |
| 2004/0147920 A1 | 7/2004 | Keidar et al. | |
| 2004/0225285 A1 | 11/2004 | Gibson | |
| 2005/0059862 A1* | 3/2005 | Phan | A61B 18/1482 |
| | | | 600/128 |
| 2005/0070887 A1 | 3/2005 | Taimisto et al. | |
| 2005/0119686 A1 | 6/2005 | Clubb | |
| 2006/0013595 A1 | 1/2006 | Trezza et al. | |
| 2006/0106375 A1 | 5/2006 | Werneth et al. | |
| 2006/0135953 A1 | 6/2006 | Kania et al. | |
| 2007/0005092 A1 | 1/2007 | Godin et al. | |
| 2007/0071792 A1 | 3/2007 | Varner et al. | |
| 2007/0080322 A1 | 4/2007 | Walba | |
| 2007/0083194 A1 | 4/2007 | Kunis et al. | |
| 2007/0276212 A1 | 11/2007 | Fuimaono et al. | |
| 2007/0287994 A1 | 12/2007 | Patel | |
| 2008/0018891 A1 | 1/2008 | Hell et al. | |
| 2008/0021313 A1 | 1/2008 | Eidenschink et al. | |
| 2008/0051707 A1 | 2/2008 | Phan et al. | |
| 2008/0140072 A1 | 6/2008 | Stangenes et al. | |
| 2008/0161797 A1 | 7/2008 | Wang et al. | |
| 2008/0183132 A1 | 7/2008 | Davies et al. | |
| 2008/0188912 A1 | 8/2008 | Stone et al. | |
| 2008/0202637 A1 | 8/2008 | Hector et al. | |
| 2008/0208186 A1 | 8/2008 | Slater | |
| 2008/0249463 A1 | 10/2008 | Pappone et al. | |
| 2008/0249527 A1 | 10/2008 | Couture | |
| 2008/0262489 A1 | 10/2008 | Steinke | |
| 2008/0281312 A1 | 11/2008 | Werneth et al. | |
| 2009/0163890 A1 | 6/2009 | Clifford et al. | |
| 2009/0171274 A1* | 7/2009 | Harlev | A61B 5/6859 |
| | | | 604/95.04 |
| 2009/0182318 A1 | 7/2009 | Abboud et al. | |
| 2009/0270850 A1 | 10/2009 | Zhou et al. | |
| 2010/0069836 A1 | 3/2010 | Satake | |
| 2010/0114269 A1 | 5/2010 | Wittenberger et al. | |
| 2010/0160906 A1* | 6/2010 | Jarrard | A61B 18/1492 |
| | | | 606/41 |
| 2010/0204560 A1 | 8/2010 | Salahieh et al. | |
| 2010/0256629 A1 | 10/2010 | Wylie et al. | |
| 2010/0324552 A1 | 12/2010 | Kauphusman et al. | |
| 2011/0118632 A1 | 5/2011 | Sinelnikov et al. | |
| 2011/0130648 A1 | 6/2011 | Beeckler et al. | |
| 2011/0282338 A1 | 11/2011 | Fojtik | |
| 2011/0295248 A1 | 12/2011 | Wallace et al. | |
| 2011/0301587 A1 | 12/2011 | Deem et al. | |
| 2011/0313286 A1 | 12/2011 | Whayne et al. | |
| 2012/0019107 A1 | 1/2012 | Gabl et al. | |
| 2012/0029511 A1 | 2/2012 | Smith et al. | |
| 2012/0065503 A1 | 3/2012 | Rogers et al. | |
| 2012/0071870 A1 | 3/2012 | Salahieh et al. | |
| 2012/0079427 A1 | 3/2012 | Carmichael et al. | |
| 2012/0101413 A1 | 4/2012 | Beetel et al. | |
| 2012/0101538 A1 | 4/2012 | Ballakur et al. | |
| 2012/0143177 A1 | 6/2012 | Avitall | |
| 2012/0143293 A1 | 6/2012 | Mauch et al. | |
| 2012/0191079 A1 | 7/2012 | Moll et al. | |
| 2012/0209260 A1 | 8/2012 | Lambert et al. | |
| 2013/0085360 A1 | 4/2013 | Grunewald | |
| 2013/0090649 A1 | 4/2013 | Smith et al. | |
| 2013/0109982 A1 | 5/2013 | Sato et al. | |
| 2013/0150693 A1 | 6/2013 | D'Angelo et al. | |
| 2013/0165916 A1 | 6/2013 | Mathur et al. | |
| 2013/0165925 A1 | 6/2013 | Mathur et al. | |
| 2013/0165941 A1 | 6/2013 | Murphy | |
| 2013/0165990 A1* | 6/2013 | Mathur | A61N 1/06 |
| | | | 607/101 |
| 2013/0169624 A1 | 7/2013 | Bourier et al. | |
| 2013/0184702 A1 | 7/2013 | Neal, II et al. | |
| 2013/0261692 A1 | 10/2013 | Cardinal et al. | |
| 2013/0274562 A1 | 10/2013 | Ghaffari et al. | |
| 2013/0274658 A1 | 10/2013 | Steinke et al. | |
| 2013/0282084 A1 | 10/2013 | Mathur et al. | |
| 2013/0318439 A1 | 11/2013 | Landis et al. | |
| 2014/0012242 A1 | 1/2014 | Lee et al. | |
| 2014/0018788 A1* | 1/2014 | Engelman | A61B 18/1492 |
| | | | 606/33 |
| 2014/0031813 A1 | 1/2014 | Tellio et al. | |
| 2014/0058197 A1* | 2/2014 | Salahieh | A61M 25/1011 |
| | | | 600/109 |
| 2014/0121470 A1 | 5/2014 | Scharf et al. | |
| 2014/0148805 A1 | 5/2014 | Stewart et al. | |
| 2014/0227437 A1 | 8/2014 | Deboer et al. | |
| 2014/0243821 A1 | 8/2014 | Salahieh et al. | |
| 2014/0257280 A1 | 9/2014 | Hanson et al. | |
| 2014/0275993 A1 | 9/2014 | Ballakur | |
| 2014/0276756 A1 | 9/2014 | Hill | |
| 2014/0276811 A1 | 9/2014 | Koblish et al. | |
| 2014/0288546 A1 | 9/2014 | Sherman et al. | |
| 2014/0330266 A1 | 11/2014 | Thompson et al. | |
| 2014/0357956 A1 | 12/2014 | Salahieh et al. | |
| 2014/0378803 A1 | 12/2014 | Geistert et al. | |
| 2015/0005799 A1 | 1/2015 | Lindquist et al. | |
| 2015/0018818 A1 | 1/2015 | Willard et al. | |
| 2015/0025532 A1* | 1/2015 | Hanson | A61B 18/1492 |
| | | | 156/60 |
| 2015/0025533 A1 | 1/2015 | Groff et al. | |
| 2015/0057655 A1 | 2/2015 | Osypka | |
| 2015/0067512 A1 | 3/2015 | Roswell | |
| 2015/0080883 A1 | 3/2015 | Haverkost et al. | |
| 2015/0105774 A1 | 4/2015 | Lindquist et al. | |
| 2015/0112256 A1 | 4/2015 | Byrne et al. | |
| 2015/0112321 A1 | 4/2015 | Cadouri | |
| 2015/0119875 A1 | 4/2015 | Fischell et al. | |
| 2015/0119877 A1 | 4/2015 | Jameson et al. | |
| 2015/0141982 A1 | 5/2015 | Lee | |
| 2015/0157382 A1 | 6/2015 | Avitall et al. | |
| 2015/0216591 A1 | 8/2015 | Cao et al. | |
| 2015/0216650 A1 | 8/2015 | Shaltis | |
| 2015/0265329 A1 | 9/2015 | Lalonde et al. | |
| 2015/0265339 A1 | 9/2015 | Lindquist et al. | |
| 2015/0265812 A1 | 9/2015 | Lalonde | |
| 2015/0272667 A1* | 10/2015 | Govari | A61B 18/1492 |
| | | | 606/41 |
| 2015/0327805 A1 | 11/2015 | Ben-Haim | |
| 2015/0341752 A1 | 11/2015 | Flynn | |
| 2016/0000499 A1 | 1/2016 | Lennox et al. | |
| 2016/0051321 A1 | 2/2016 | Salahieh et al. | |
| 2016/0085431 A1 | 3/2016 | Kim et al. | |
| 2016/0106499 A1 | 4/2016 | Ogata et al. | |
| 2016/0166306 A1 | 6/2016 | Pageard | |
| 2016/0175041 A1 | 6/2016 | Govari et al. | |
| 2016/0183877 A1 | 6/2016 | Williams et al. | |
| 2016/0196635 A1 | 7/2016 | Cho et al. | |
| 2016/0256305 A1 | 9/2016 | Longo et al. | |
| 2016/0374748 A9 | 12/2016 | Salahieh et al. | |
| 2017/0042614 A1 | 2/2017 | Salahieh et al. | |

(56) References Cited

U.S. PATENT DOCUMENTS

| | | | |
|---|---|---|---|
| 2017/0042615 A1 | 2/2017 | Salahieh et al. | |
| 2017/0080192 A1 | 3/2017 | Giasolli et al. | |
| 2017/0143359 A1 | 5/2017 | Nguyen et al. | |
| 2017/0164464 A1 | 6/2017 | Weinkam et al. | |
| 2017/0311829 A1 | 11/2017 | Beeckler et al. | |
| 2017/0311893 A1 | 11/2017 | Beeckler et al. | |
| 2017/0312022 A1 | 11/2017 | Beeckler et al. | |
| 2017/0347896 A1 | 12/2017 | Keyes et al. | |
| 2017/0348049 A1 | 12/2017 | Vrba et al. | |
| 2017/0354467 A1 | 12/2017 | Rankin et al. | |
| 2018/0074693 A1 | 3/2018 | Jones et al. | |
| 2018/0092688 A1 | 4/2018 | Tegg | |
| 2018/0110562 A1 | 4/2018 | Govari et al. | |
| 2018/0125575 A1 | 5/2018 | Schwartz et al. | |
| 2018/0161093 A1 | 6/2018 | Basu et al. | |
| 2018/0256247 A1 | 9/2018 | Govari et al. | |
| 2018/0333162 A1 | 11/2018 | Saab | |
| 2018/0368927 A1 | 12/2018 | Lyons et al. | |
| 2019/0117303 A1 | 4/2019 | Claude et al. | |
| 2019/0297441 A1 | 9/2019 | Dehe et al. | |
| 2019/0298441 A1 | 10/2019 | Clark et al. | |
| 2020/0001054 A1 | 1/2020 | Jimenez et al. | |
| 2020/0008869 A1 | 1/2020 | Byrd | |
| 2020/0015693 A1 | 1/2020 | Beeckler et al. | |
| 2020/0046422 A1 | 2/2020 | Bishara et al. | |
| 2020/0085497 A1 | 3/2020 | Zhang et al. | |
| 2020/0155226 A1 | 5/2020 | Valls et al. | |
| 2021/0169567 A1 | 6/2021 | Govari et al. | |

FOREIGN PATENT DOCUMENTS

| | | | |
|---|---|---|---|
| CN | 102106752 A | 6/2011 | |
| CN | 102271607 A | 12/2011 | |
| CN | 102458566 A | 5/2012 | |
| CN | 103118613 A | 5/2013 | |
| CN | 203539434 U | 4/2014 | |
| CN | 104244856 A | 12/2014 | |
| CN | 104546117 A | 4/2015 | |
| CN | 104939916 A | 9/2015 | |
| CN | 105105844 A | 12/2015 | |
| CN | 105473091 A | 4/2016 | |
| CN | 105473093 A | 4/2016 | |
| CN | 106572842 A | 4/2017 | |
| CN | 107970065 A | 5/2018 | |
| CN | 108175400 A | 6/2018 | |
| EP | 0779059 A1 | 6/1997 | |
| EP | 1790304 A2 | 5/2007 | |
| EP | 2865350 A2 | 4/2015 | |
| EP | 2875790 A2 | 5/2015 | |
| EP | 3199118 A1 | 8/2017 | |
| EP | 3238646 A2 | 11/2017 | |
| EP | 3238648 A1 | 11/2017 | |
| EP | 3251622 A1 | 12/2017 | |
| EP | 3300680 A1 | 4/2018 | |
| EP | 3315087 A1 | 5/2018 | |
| EP | 3332727 A2 | 6/2018 | |
| EP | 3571983 A2 | 11/2019 | |
| EP | 3572024 A1 | 11/2019 | |
| EP | 3586778 A1 | 1/2020 | |
| EP | 3653153 A1 | 5/2020 | |
| JP | H0314121 A | 1/1991 | |
| JP | H06261951 A | 9/1994 | |
| JP | 41176233 A | 3/1999 | |
| JP | H11327735 A | 11/1999 | |
| JP | 2000504242 A | 4/2000 | |
| JP | 2002336266 A | 11/2002 | |
| JP | 2004504314 A | 2/2004 | |
| JP | 2005052424 A | 3/2005 | |
| JP | 2008538986 A | 11/2008 | |
| JP | 2009261609 A | 11/2009 | |
| JP | 2010507404 A | 3/2010 | |
| JP | 2010088697 A | 4/2010 | |
| JP | 2012024156 A | 2/2012 | |
| JP | 2012508083 A | 4/2012 | |
| JP | 2013013726 A | 1/2013 | |
| JP | 2013078587 A | 5/2013 | |
| JP | 2013529109 A | 7/2013 | |
| JP | 2014509218 A | 4/2014 | |
| JP | 2014529419 A | 11/2014 | |
| JP | 2015503365 A | 2/2015 | |
| JP | 2015100706 A | 6/2015 | |
| JP | 2015112113 A | 6/2015 | |
| JP | 2015112114 A | 6/2015 | |
| JP | 2015518776 A | 7/2015 | |
| JP | 2016093502 A | 5/2016 | |
| JP | 2016515442 A | 5/2016 | |
| JP | 2016116863 A | 6/2016 | |
| JP | 2016534842 A | 11/2016 | |
| JP | 2017202305 A | 11/2017 | |
| JP | 2017202306 A | 11/2017 | |
| JP | 2018075365 A | 5/2018 | |
| WO | 9605768 A1 | 2/1996 | |
| WO | 0056237 A2 | 9/2000 | |
| WO | 02102231 A2 | 12/2002 | |
| WO | 2005041748 A2 | 5/2005 | |
| WO | 2006055654 A1 | 5/2006 | |
| WO | 2008049087 A2 | 4/2008 | |
| WO | 2011143468 A2 | 11/2011 | |
| WO | 2013049601 A2 | 4/2013 | |
| WO | 2013052919 A2 | 4/2013 | |
| WO | 2013154776 A2 | 10/2013 | |
| WO | 2014123983 A2 | 8/2014 | |
| WO | 2014168987 A1 | 10/2014 | |
| WO | 2015049784 A1 | 4/2015 | |
| WO | 2015200518 A1 | 12/2015 | |
| WO | 2016084215 A1 | 6/2016 | |
| WO | 2016183337 A2 | 11/2016 | |
| WO | 2016210437 A1 | 12/2016 | |
| WO | 2017024306 A1 | 2/2017 | |
| WO | 2017087549 A1 | 5/2017 | |
| WO | 2017163400 A1 | 9/2017 | |
| WO | 2018106569 A1 | 6/2018 | |
| WO | 2019095020 A1 | 5/2019 | |
| WO | 2019156195 A1 | 8/2019 | |

OTHER PUBLICATIONS

YouTube, "New Interface TactiCath Contact Force Ablation Catheter", Nov. 26, 2013, retrieved from internet [https://www.youtube.com/watch?v=aYvYO8Hpylg], retrieved on Nov. 19, 2020, 1 page.

European Search Report for European Application No. 19183327, mailed on Nov. 21, 2019, 8 pages.

Extended European Search Report for European Application No. EP19177365.4, mailed on Nov. 8, 2019, 7 pages.

Haines, D.E., et al., "The Promise of Pulsed Field Ablation," Dec. 2019, vol. 19 (12), pp. 10.

Extended European Search Report for European Application No. EP20153872.5, mailed on May 7, 2020, 8 pages.

Extended European Search Report for European Application No. EP20195648.9, mailed on Feb. 12, 2021, 8 pages.

International Search Report and Written Opinion for Application No. PCT/IB2019/056381, mailed on Dec. 17, 2019, 10 pages.

Compounding Solutions, "PEBA RO Compounds", Nov. 17, 2017 (Year: 2017), 1 page.

Compounding Solutions, "Vestamid Care ML", Jul. 28, 2019 (Year: 2019), 1 page.

Demetrius Lopes, Balloon Design and Performance: Presentation of various types of balloons on the market. Attached. Also available at: https://www.neurovascularexchange.com/media/slides/210/balloon-design-and-performance-presentation-of-various-types-of-balloons-on-the-market.pdf, 2016, 80 pages.

Foster, "Foster Corporation Introduces Newest ProPellTM "T" Translucent Compounds", Sep. 13, 2018 (Year: 2018), 3 pages.

Foster, "Foster ProPellTM "T" Low Friction Compounds", 2018 (Year: 2018), 2 pages.

Medtronic, Hyper Occlusion Balloon Portfolio. Attached. Also Available at: https://www.linnc.com/content/download/125103/2591577/version/1/file/Hyper+Balloon+Brochure+LR.pdf, 2017, 3 pages.

(56)     References Cited

OTHER PUBLICATIONS

Extended European Search Report for Application No. EP17168393.1 mailed on Dec. 15, 2017, 12 pages.
Extended European Search Report for Application No. EP17168513.4 mailed on Sep. 18, 2017, 11 pages.
Extended European Search Report for European Application No. 17201434.2, mailed on Feb. 1, 2018, 9 pages.
Extended European Search Report for European Application No. EP15201723.2, mailed on May 11, 2016, 7 pages.
Extended European Search Report for European Application No. EP17168518.3, mailed on Sep. 20, 2017, 9 pages.
Extended European Search Report for European Application No. EP17173893.3, mailed on Nov. 6, 2017, 8 pages.
Extended European Search Report for European Application No. EP17205876.0, mailed on Jun. 1, 2018, 13 pages.
International Search Report and Written Opinion for Application No. PCT/IB2019/052313, mailed on Jul. 22, 2019, 08 pages.
Partial European Search Report for Application No. EP17168393.1 mailed on Sep. 13, 2017, 13 pages.
Partial European Search Report for European Application No. EP17205876.0, mailed on Feb. 22, 2018, 10 pages.

\* cited by examiner

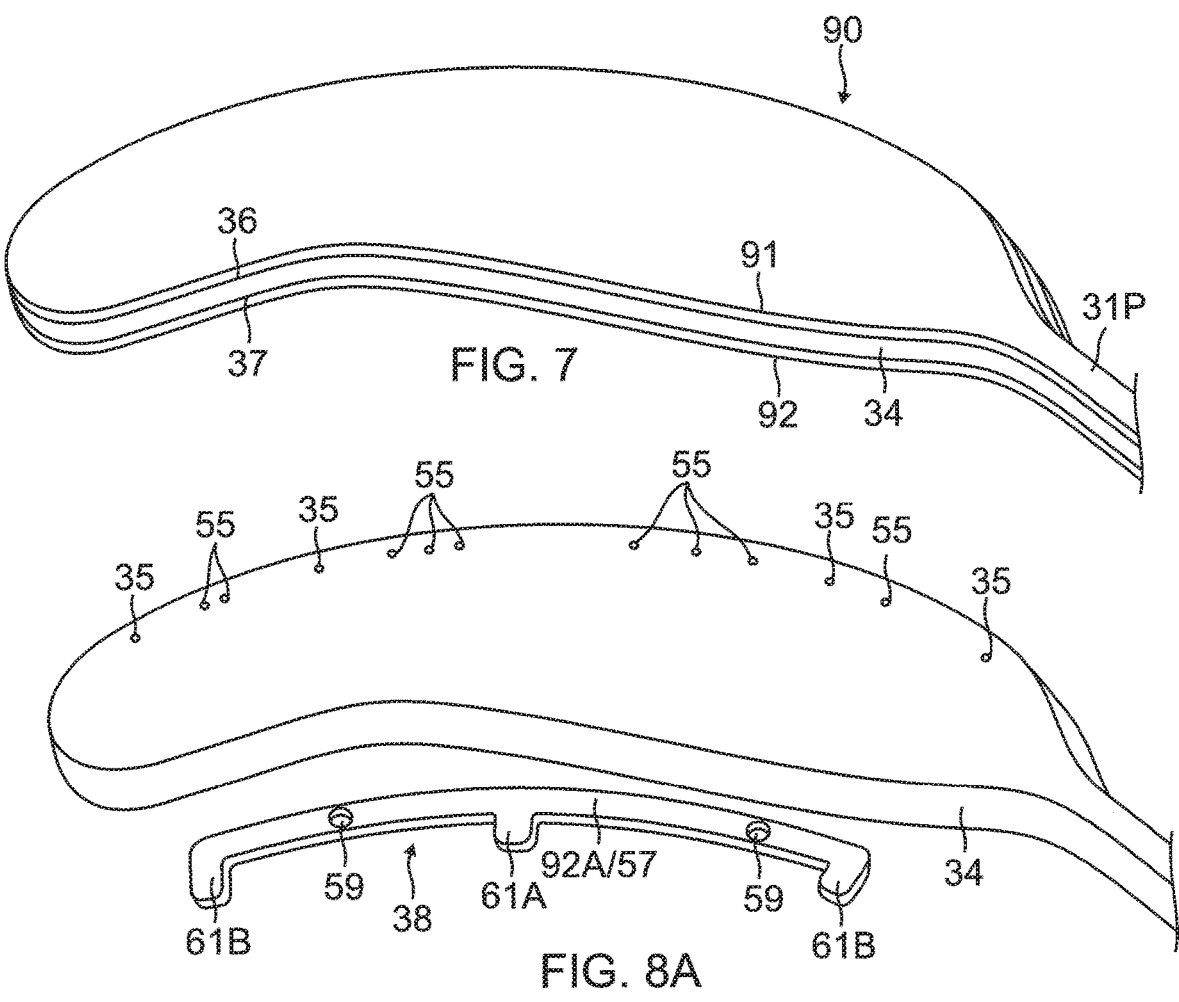
FIG. 7
FIG. 8A
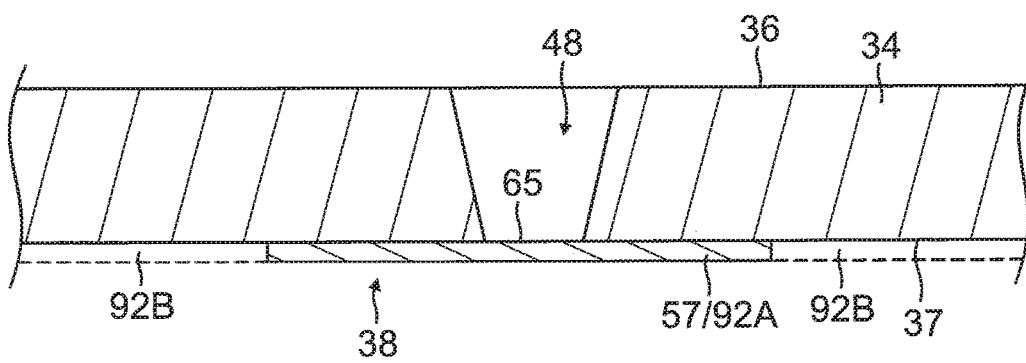
FIG. 8B

IRRIGATED BALLOON CATHETER WITH FLEXIBLE CIRCUIT ELECTRODE ASSEMBLY

CROSS REFERENCE TO RELATED APPLICATIONS

The present application is a Continuation Application under 35 U.S.C. § 120 of U.S. patent application Ser. No. 15/360,964, filed Nov. 23, 2016 and issued as U.S. Pat. No. 10,653,480, and U.S. patent application Ser. No. 15/360, 966, filed Nov. 23, 2016 and issued as U.S. Pat. No. 10,660,700. Both of these applications are Continuation-In-Part Applications under 35 U.S.C. § 120 of U.S. patent application Ser. No. 15/141,751, filed Apr. 28, 2016 and issued as U.S. Pat. No. 10,638,976, and U.S. patent application Ser. No. 15/172,118, filed Jun. 2, 2016, now abandoned. The entire contents of these four applications is incorporated by reference herein in its entirety.

FIELD OF INVENTION

This invention relates to medical devices. More particularly, this invention relates to improvements in cardiac catheterization, including electrophysiologic (EP) catheters, in particular, EP catheters for mapping and/or ablating ostia and tubular regions in the heart.

BACKGROUND

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

Circumferential lesions at or near the ostia of the pulmonary veins have been created to treat atrial arrhythmias. U.S. Pat. Nos. 6,012,457 and 6,024,740, both to Lesh, disclose a radially expandable ablation device, which includes a radiofrequency electrode. Using this device, it is proposed to deliver radiofrequency energy to the pulmonary veins in order to establish a circumferential conduction block, thereby electrically isolating the pulmonary veins from the left atrium.

U.S. Pat. No. 6,814,733 to Schwartz et al., which is commonly assigned herewith and herein incorporated by reference, describes a catheter introduction apparatus having a radially expandable helical coil as a radiofrequency emitter. In one application the emitter is introduced percutaneously, and transseptally advanced to the ostium of a pulmonary vein. The emitter is radially expanded, which can be accomplished by inflating an anchoring balloon about which the emitter is wrapped, in order to cause the emitter to make circumferential contact with the inner wall of the pulmonary vein. The coil is energized by a radiofrequency generator, and a circumferential ablation lesion is produced in the myocardial sleeve of the pulmonary vein, which effectively blocks electrical propagation between the pulmonary vein and the left atrium.

Another example is found in U.S. Pat. No. 7,340,307 to Maguire, et al., which proposes a tissue ablation system and method that treats atrial arrhythmia by ablating a circumferential region of tissue at a location where a pulmonary vein extends from an atrium. The system includes a circumferential ablation member with an ablation element and includes a delivery assembly for delivering the ablation member to the location. The circumferential ablation member is generally adjustable between different configurations to allow both the delivery through a delivery sheath into the atrium and the ablative coupling between the ablation element and the circumferential region of tissue.

More recently, inflatable catheter electrode assemblies have been constructed with flex circuits to provide the outer surface of the inflatable electrode assemblies with a multitude of very small electrodes. Examples of catheter balloon structures are described in U.S. Publication No. 2016/0175041, titled Balloon for Ablation Around Pulmonary Vein, the entire content of which is incorporated herein by reference.

Flex circuits or flexible electronics involve a technology for assembling electronic circuits by mounting electronic devices on flexible plastic substrates, such as polyimide, Liquid Crystal Polymer (LCP), PEEK or transparent conductive polyester film (PET). Additionally, flex circuits can be screen printed silver circuits on polyester. Flexible printed circuits (FPC) are made with a photolithographic technology. An alternative way of making flexible foil circuits or flexible flat cables (FFCs) is laminating very thin (0.07 mm) copper strips in between two layers of PET. These PET layers, typically 0.05 mm thick, are coated with an adhesive which is thermosetting, and will be activated during the lamination process. Single-sided flexible circuits have a single conductor layer made of either a metal or conductive (metal filled) polymer on a flexible dielectric film. Component termination features are accessible only from one side. Holes may be formed in the base film to allow component leads to pass through for interconnection, normally by soldering.

However, due to variances in human anatomy, ostia and tubular regions in the heart come in all sizes. Thus, conventional balloon or inflatable catheters may not have necessary flexibility to accommodate different shapes and sizes while having sufficient structural support for effective circumferential contact with tissue. In particular, ablation electrodes that provide greater surface contact may lack sufficient flexibility. Moreover, delicate wires such as those of electrode lead wires and/or thermocouple wires and their solder joints need support and protection from breakage and damage during both assembly and use in the patient's body. Additionally, because the balloon configuration is radially symmetrical and multiple electrode elements surround the balloon configuration, determining the orientation of the balloon electrode assembly under fluoroscopy has also posed challenges.

Accordingly, there is a desire for a balloon or a catheter having an inflatable member with contact electrodes that can contact more tissue area while remaining sufficiently flexible to accommodate different anatomy and the tighter space constraints of an ostium and a pulmonary vein. There is also a desire for a balloon catheter to carry an electrode assembly with adaptations for the ostium and pulmonary vein that can be manufactured from a generic flexible circuit. There is a further desire for a balloon catheter capable of multiple functions including diagnostic and therapeutic functions, such as ablation, pacing, navigation, temperature sensing, electropotential sensing and impedance sensing, and be adaptive for use with other catheters, including a lasso catheter or a focal catheter.

SUMMARY OF THE INVENTION

The present invention is directed to a catheter having an irrigated inflatable balloon adapted for use in an ostium of a pulmonary vein. The balloon includes a flexible circuit electrode assembly adapted for circumferential contact with the ostium when the balloon is inflated. The balloon catheter is well suited for both diagnostic and therapeutic applications and procedures and may be used with a lasso catheter or focal catheter.

In some embodiments, an electrophysiology catheter adapted for use in an ostium, includes a balloon having an membrane, the balloon having a distal end and a proximal end defining a longitudinal axis; and a contact electrode supported on the membrane, the contact electrode configured for contact with the ostium, the contact electrode having a "fishbone" configuration with a longitudinally elongated portion and a plurality of transversal fingers.

In some more detailed embodiments, the transversal fingers have different lengths and the contact electrode has longer fingers and shorter fingers, the longer fingers being situated near an equatorial region of the balloon. Moreover, the plurality of fingers may include a distal finger, a proximal finger and fingers in between, wherein each of the fingers in between has a shorter adjacent finger. A width of the elongated portion may be greater than a width of each finger. The plurality of fingers may be generally evenly spaced along the elongated portion. The plurality of fingers may have a generally uniform width.

In some more detailed embodiments, the contact electrode comprises gold. The contact electrode may include a seed layer below the gold. A balloon may have a plurality of contact electrodes generally evenly radially distributed on its membrane.

In some embodiments, an electrophysiology catheter includes a balloon with a membrane, and a flex circuit electrode assembly on the membrane. The flex circuit has a substrate having a first surface and a second surface, a contact electrode on the first surface, a wiring electrode on the second surface, and a conductive via extending through the substrate and adapted to conductively connect the contact electrode and the wiring electrode.

In some more detailed embodiments, the substrate includes a first irrigation aperture, the membrane includes a second irrigation aperture aligned with the first irrigation aperture. Moreover, the contact electrode may include an exclusion zone surrounding the first irrigation aperture, and the wiring electrode may include an exclusion zone surrounding the first irrigation aperture. The wiring electrode may have an elongated body longitudinally aligned with the elongated portion. The wiring electrode may include a solder pad, wherein the flex circuit electrode assembly includes a wire pair conductively connected to the solder pad.

In additional more detailed embodiments, the flex circuit electrode includes a "fishbone" contact microelectrode, a "spine" wiring microelectrode, and a conductive via configured to conductively couple the contact microelectrode and the wiring electrode. The microelectrodes are strategically positioned relative to the electrodes to be close and proximate thereto but yet be physically and electrically isolated therefrom. The flex circuit electrode includes at least one exclusion zone configured to physically and electrically isolate the microelectrodes from the contact electrode and the wiring electrode. A microelectrode may be configured as an "island" surrounded circumferentially in its entirety by a contact electrode or a wiring electrode and physically and electrically isolated therefrom by an exclusion zone.

In some embodiments, the flex circuit electrode includes a proximal tail. Conductive wires configured for conductive connection to the contact electrode and/or the wiring electrode may extend between the proximal tail and the balloon membrane toward a shaft of the balloon catheter. In some embodiments, the conductive wires may extend through a through-hole formed in the balloon membrane to enter an interior of the balloon.

In some embodiments, the contact electrode and the wiring electrode may be split into a plurality of portions, with a respective contact electrode portion and a respective wiring electrode portion being conductively coupled by a conductive via. Conductive wires are provided for each conductively connected pair of contact electrode portion and wiring electrode portion. Each split electrode portion may surround a respective microelectrode physically and electrically isolated by an exclusion zone.

In some embodiments, conductive wires configured for conductive connection to the electrodes and the microelectrodes may be included in a ribbon cable. The ribbon cable may pass into an interior of the balloon through a through-hole formed in the balloon membrane. Alternatively, the ribbon cable may extend between a tail of the flex circuit electrode assembly and the balloon membrane toward proximal end of the balloon before entering a shaft proximal of the balloon.

In some embodiments, the flex circuit electrode assembly includes a thermocouple for use with a contact microelectrode, where the thermocouple has a wire pair which are embedded in the flex circuit substrate and connected to each other by a conducting via conductively coupled to the contact electrode. Advantageously, the thermocouple is configured to measure temperature of tissue in contact with the contact microelectrode while undergoing ablation by adjacent ablating contact electrode. Alternatively, when the tissue is not undergoing ablation, the thermocouple can concurrently sense electropotential signals from the tissue and the temperature of the tissue.

In some embodiments, the flex circuit electrode assembly includes a first and a second solder pads conductively coupled to first and second wires of the thermocouple, the solders pad being advantageously located remotely from the microelectrode, for example, in a region of the proximal tail, wherein a potential between the first and second solder pads comprises a signal representative of a temperature sensed by the thermocouple 400 at the location of the microelectrode 401. Moreover, each the solder pad, so electrically coupled, may also acquire electropotentials formed on its respective microelectrode 401 by its conductive via.

In some embodiments, solder pads coupled to a contact electrode, a microelectrode and a thermocouple for ablation, sensing electropotentials and temperature may be grouped as a set, where a flex circuit electrode assembly includes multiple sets of solder pads, all located remotely from the microelectrodes.

In some embodiments, the balloon catheter is configured for use with a second catheter, extending through a shaft of the balloon catheter. The second catheter may include a lasso catheter or a linear focal catheter.

The present invention is also directed to methods of constructing the aforementioned balloon catheter. In some embodiments, the method of constructing a flexible circuit electrode assembly for use in assembling an electrophysiology balloon catheter adapted for use in an ostium, includes: providing a flex circuit having a substrate, a first conductive layer and a second conductive layer; removing the first conductive layer to expose a first surface of the substrate; forming the wiring electrode in the second conductive layer with one exclusion zone; forming a first through-hole in the substrate to provide one conductive via and forming a second through-hole to provide an irrigation aperture in alignment with the exclusion zone; forming the contact electrode on first surface of the substrate; and introducing conductive material into the first through-hole to form the conductive via, the conductive via extending through the substrate and electrically coupling the wiring electrode and the contact electrode. In some more detailed embodiments, the conductive material is introduced into the first through-hole during at least one of the forming the wiring electrode and the forming the contact electrode.

In some embodiments, the method further includes applying an added conductive layer on exposed conductive surfaces, after the forming the first and second through-holes in the substrate.

In some embodiments, the method further includes applying an added conductive layer on exposed conductive surfaces on the substrate, the wiring electrode and the contact electrode, after the forming the contact electrode.

In some embodiments, the method further includes conductively coupling a first and a second conductive lines of different metals to the wiring electrode.

In some embodiments, the forming the contact electrode includes applying a seed layer and applying a second added conductive layer on the first surface of the substrate. The applying the seed layer and applying a second added conductive layer may include applying the seed layer and the second added conductive layer in at least a region within a perimeter trace of the contact electrode.

In some embodiments, the method includes applying a photoresist on the first surface of the substrate on a region outside of a perimeter trace of the contact electrode, applying the seed layer on the first surface of the substrate on at least a region inside of the perimeter trace of the contact electrode, applying a second added conductive layer on the first surface of the substrate on at least the region inside of the perimeter trace of the contact electrode, and removing the photoresist from the first surface of the substrate.

In some embodiments, a method of constructing an electrophysiology catheter adapted for use in an ostium, the catheter having a balloon having an membrane and a flex circuit electrode assembly, the method including: providing a flex circuit having a substrate, a first conductive layer and a second conductive layer; removing the first conductive layer to expose a first surface of the substrate; forming the wiring electrode in the second conductive layer with one exclusion zone; forming a first through-hole in the substrate to provide one conductive via and forming a second through-hole to provide an irrigation aperture in alignment with the exclusion zone; forming the contact electrode on first surface of the substrate; placing conductive material into the first through-hole to form the conductive via, the conductive via extending through the substrate and electrically coupling the wiring electrode and the contact electrode; coupling a first conductor and a second conductor to the wiring electrode to form a thermocouple; and affixing the flex circuit to the membrane with the wiring electrode between the substrate and the membrane.

In some embodiments, the method further includes passing the first and second conductors of the thermocouple into an interior of the balloon through a through-hole formed in the membrane. In some embodiments, the method further includes placing the first and second conductors of the thermocouple between a tail of the flex circuit and the membrane.

In some embodiments, the forming the wiring electrode includes forming an active solder pad and/or forming an inactive solder pad.

In some embodiments, the forming the contact electrode includes applying a seed layer and applying a second added conductive layer on the first surface of the substrate. In some embodiments, the applying the seed layer and applying a second added conductive layer includes applying the seed layer and the second added conductive layer in at least a region within a perimeter trace of the contact electrode.

In some embodiments, the method include applying a photoresist on the first surface of the substrate on a region outside of a perimeter trace of the contact electrode, applying the seed layer on the first surface of the substrate on at least a region inside of the perimeter trace of the contact electrode, applying a second added conductive layer on the first surface of the substrate on at least the region inside of the perimeter trace of the contact electrode, and removing the photoresist from the first surface of the substrate.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIGS. 7, 8A, 9A, 10, 11A, 12A, 13A are exploded perspective views of a flexible circuit electrode assembly in different stages of construction, according to an embodiment of the present invention.

FIGS. 8B, 9B, 11B, 12B, 13B, 14 are side cross-sectional views of a flexible circuit electrode assembly in different stages of construction, according to an embodiment of the present invention.

DETAILED DESCRIPTION OF THE INVENTION

Overview

Figure 1:
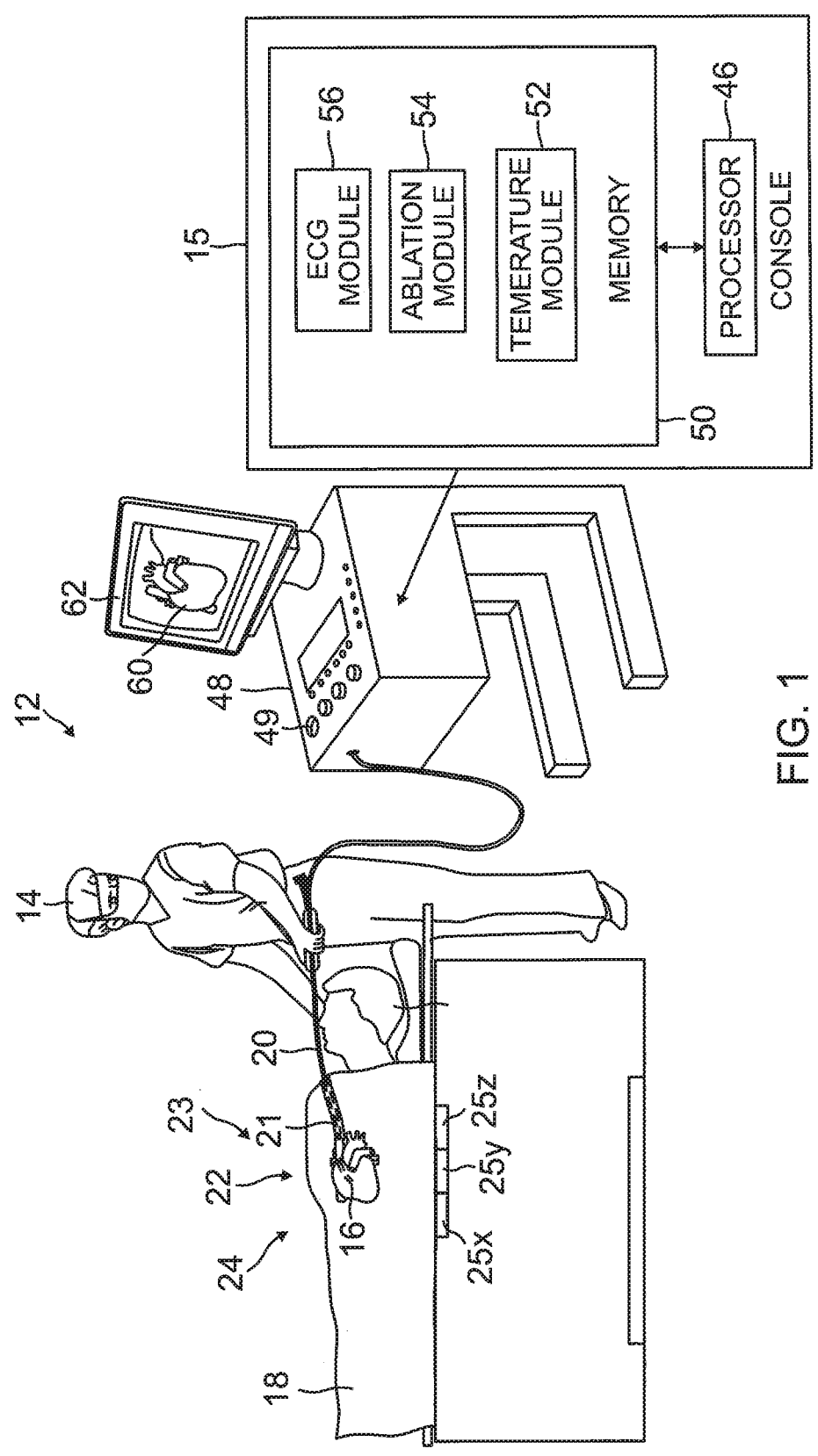
FIG. 1 is a schematic illustration of an invasive medical procedure, according to an embodiment of the present invention.

Ablation of cardiac tissue to correct a malfunctioning heart is a well-known procedure for implementing such a correction. Typically, in order to successfully ablate, cardia electropotentials need to be measured at various locations of the myocardium. In addition, temperature measurements during ablation provide data enabling the efficacy of the ablation to be measured. Typically, for an ablation procedure, the electropotentials and the temperatures are measured before, during, and after the actual ablation.

In contrast with prior art systems that use two or more separate instructions (e.g., one for the electropotential and temperature measurements, and another for the ablation), embodiments of the present invention facilitate the two measurements, and in addition enable ablation using radiofrequency electromagnetic energy, using a single balloon catheter. The catheter has a lumen, and an inflatable balloon is deployed through the catheter lumen (the balloon travels through the lumen in a collapsed, uninflated configuration, and the balloon is inflated on exiting the lumen). The balloon has an exterior wall or membrane and has a distal end and a proximal end which define a longitudinal axis that extends the lumen.

A multi-layer flexible metal structure is attached to an exterior wall or membrane of the balloon. The structure comprises a plurality of electrode groups arranged circumferentially about the longitudinal axis, where each electrode group comprises multiple ablation electrodes, typically arranged longitudinally.

Each electrode group may also include at least one micro-electrode that is insulated physically and electrically from the ablation electrodes in its group.

Each electrode group may also include at least a thermocouple.

In some embodiments, each electrode group has a micro-electrode and a thermocouple formed at a common location.

Using a single balloon catheter, with the three functionalities of ability to perform ablation, electropotential measurement, and temperature measurement, simplifies cardiac ablation procedures.

System Description

In the following description, like elements in the drawings are identified by like numerals, and like elements are differentiated as necessary by appending a letter to the identifying numeral.

FIG. 1 is a schematic illustration of an invasive medical procedure using apparatus 12, according to an embodiment of the present invention. The procedure is performed by a medical professional 14, and, by way of example, the procedure in the description hereinbelow is assumed to comprise ablation of a portion of a myocardium 16 of the heart of a human patient 18. However, it is understood that embodiments of the present invention are not merely applicable to this specific procedure, and may include substantially any procedure on biological tissue or on non-biological materials.

Figure 2:
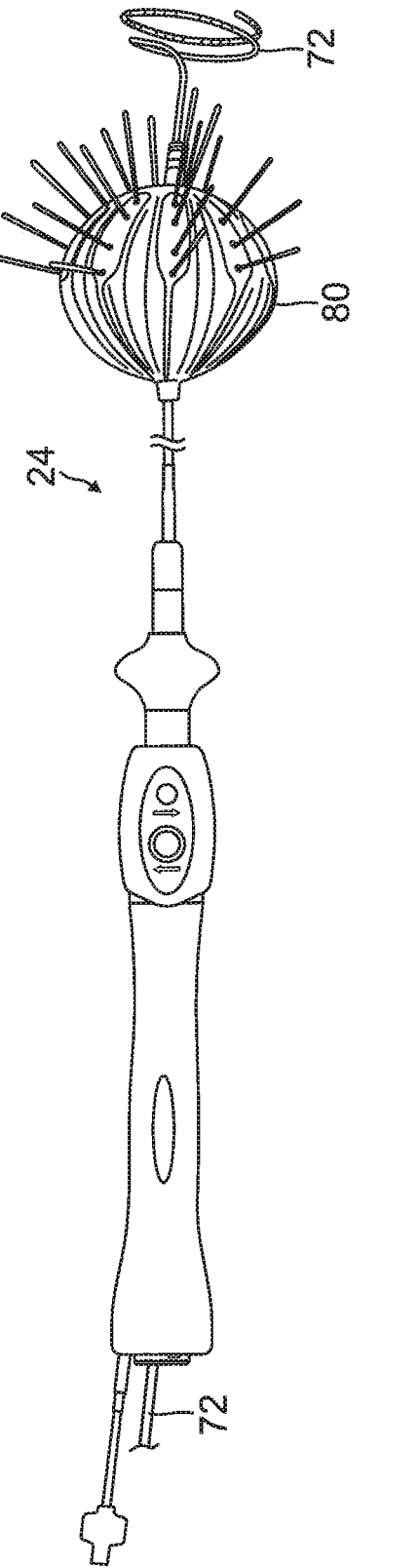
FIG. 2 is a top view of a balloon catheter of the present invention in its inflated state, in use with a lasso catheter, according to an embodiment of the present invention.

In order to perform the ablation, medical professional 14 inserts a probe 20 into a sheath 21 that has been pre-positioned in a lumen of the patient. Sheath 21 is positioned so that a distal end 22 of probe 20 enters the heart of the patient. A balloon catheter 24, which is described in more detail below with reference to FIG. 2, is deployed through a lumen 23 of the probe 20, and exits from a distal end of the probe 20.

As shown in FIG. 1, apparatus 12 is controlled by a system processor 46, which is located in an operating console 15 of the apparatus. Console 15 comprises controls 49 which are used by professional 14 to communicate with the processor. During the procedure, the processor 46 typically tracks a location and an orientation of the distal end 22 of the probe 20, using any method known in the art. For example, processor 46 may use a magnetic tracking method, wherein magnetic transmitters 25X, 25Y and 25Z external to the patient 18 generate signals in coils positioned in the distal end of the probe 20. The CARTO® available from Biosense Webster, Inc. of Diamond Bar, California, uses such a tracking method.

The software for the processor 46 may be downloaded to the processor in electronic form, over a network, for example. Alternatively or additionally, the software may be provided on non-transitory tangible media, such as optical, magnetic, or electronic storage media. The tracking of the distal end 22 is typically displayed on a three-dimensional representation 60 of the heart of the patient 18 on a screen 62.

In order to operate apparatus 12, the processor 46 communicates with a memory 50, which has a number of modules used by the processor to operate the apparatus. Thus, the memory 50 comprises a temperature module 52, an ablation module 54, and an electrocardiograph (ECG) module 56, the functions of which are described below. The memory 50 typically comprises other modules, such as a force module for measuring the force on the distal end 22, a tracking module for operating the tracking method used by the processor 46, and an irrigation module allowing the processor to control irrigation provided for the distal end 22. For simplicity, such other modules are not illustrated in FIG. 1. The modules may comprise hardware as well as software elements.

Figure 3:
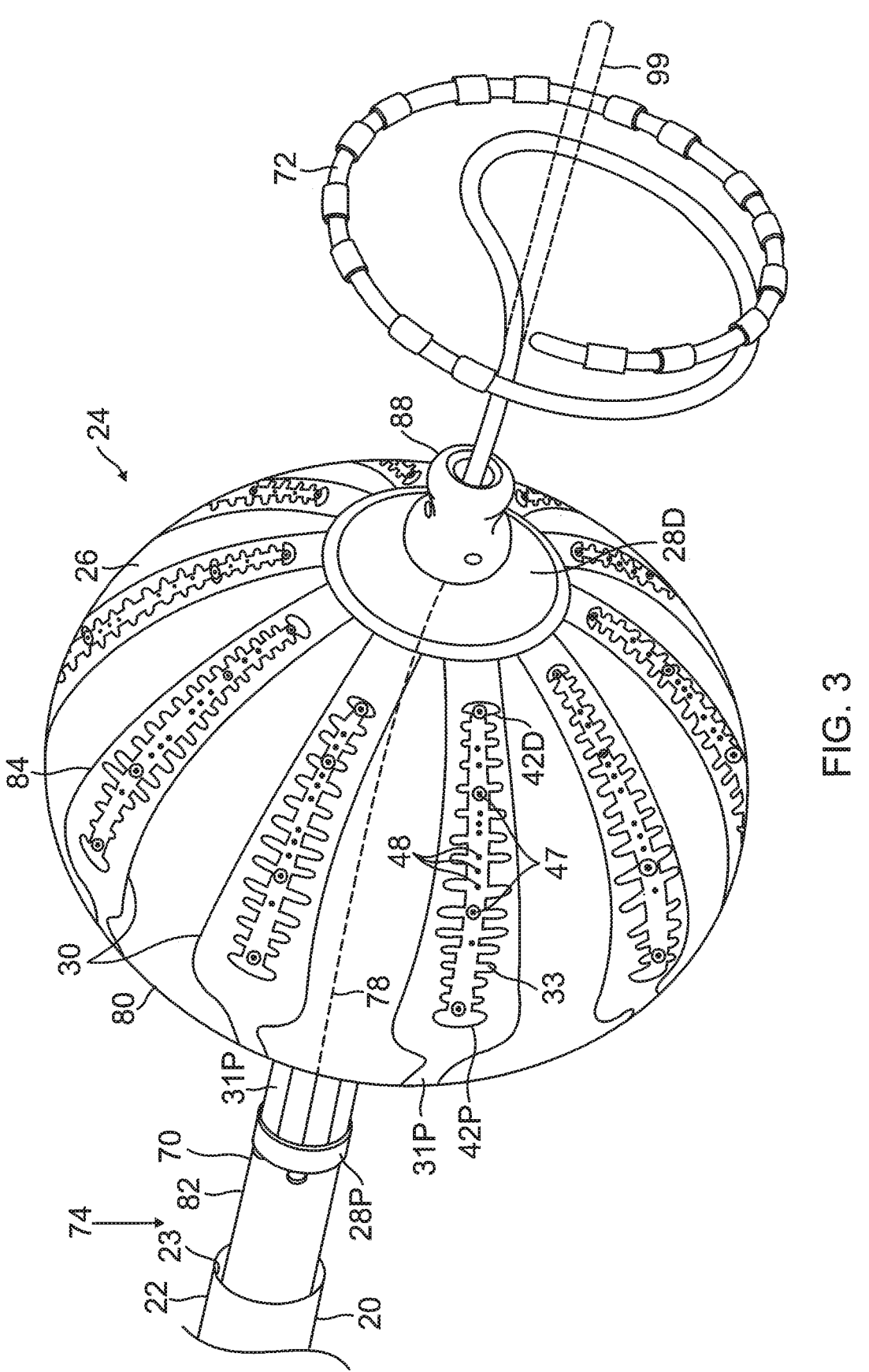
FIG. 3 is a perspective view of a balloon of the balloon catheter of FIG. 2, along with the lasso catheter.
Figure 4:
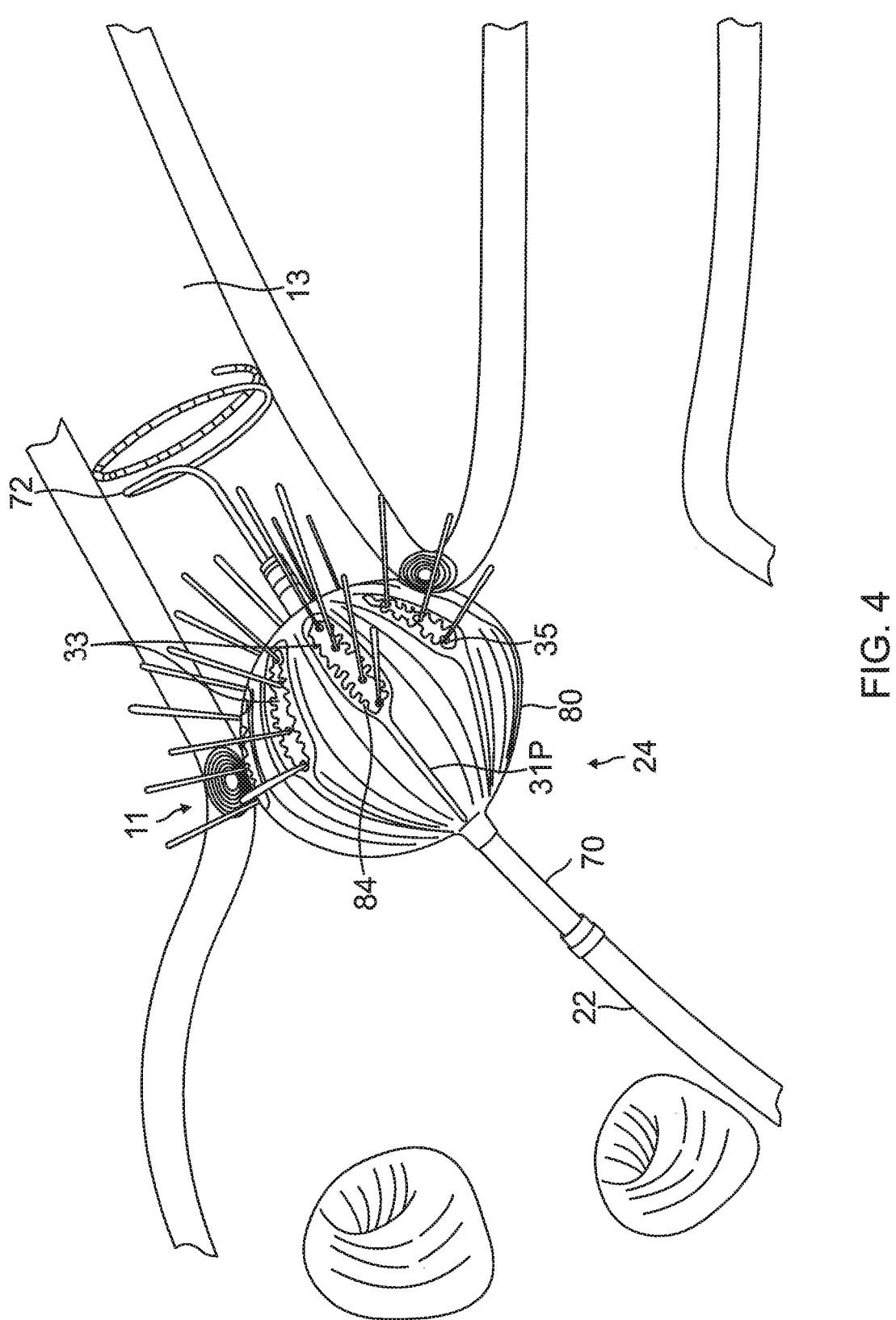
FIG. 4 is a side view of the balloon deployed in the region of a pulmonary vein and its ostium.

FIG. 3 is a schematic perspective view of the balloon catheter 24 in its inflated configuration, according to an embodiment of the present invention. In a disclosed embodiment, where the balloon catheter 24 is used to ablate an ostium 11 of a lumen, such as a pulmonary vein 13, as shown in FIG. 4, the balloon catheter 24 is supported by a tubular shaft 70 having a proximal shaft portion 82 and a distal shaft end 88. The shaft 70 comprises a hollow central tube 74, which permits a catheter to pass therethrough and past the distal shaft end 88. The catheter may be a focal linear catheter or a lasso catheter 72, as illustrated. The lasso catheter 72 may be inserted into the pulmonary vein to position the balloon catheter 24 correctly with respect to the ostium prior to ablation of the ostium. The distal lasso portion of the catheter 72 is typically formed of shape-memory retentive material such as nitinol. It is understood that the balloon catheter 24 may also be used with a linear or focal catheter 99 (as shown in broken lines in FIG. 3) in the PV or elsewhere in the heart. The focal catheter 99 may include a force sensor at its distal tip. Suitable force sending distal tips are disclosed in U.S. Pat. No. 8,357,152, issued on Jan. 22, 2013 to Govari et al., titled CATHETER WITH PRESSURE SENSING, and in U.S. Patent Application 2011/0130648, to Beeckler et al., filed Nov. 30, 2009, titled CATHETER WITH PRESSURE MEASURING TIP, the entire contents of both of which are incorporated herein by reference. Any catheter used in conjunction with the balloon catheter may have features and functions, including, for example, pressure sensing, ablation, diagnostic, e.g., navigation and pacing.

The inflatable balloon 80 of the balloon catheter 24 has an exterior wall or membrane 26 of a bio-compatible material, for example, formed from a plastic such as polyethylene terephthalate (PET), polyurethane or PEBAX®. The shaft 70 and the distal shaft end 88 define a longitudinal axis 78 of the balloon 80. The balloon 80 is deployed, in a collapsed uninflated configuration, via the lumen 23 of the probe 20, and may be inflated after existing from the distal end 22. The balloon 80 may be inflated and deflated by injection and expulsion of a fluid such as saline solution through the shaft 70. The membrane 26 of the balloon 80 is formed with irrigation pores or apertures 27 (shown in FIG. 6) through which the fluid can exit from the interior of the balloon 80 to outside the balloon for cooling the tissue ablation site at the ostium. While FIG. 2 and FIG. 4 show fluid exiting the balloon 80 as jet streams, it is understood that the fluid may exit the balloon with any desired flow rate and/or pressure, including a rate where the fluid is seeping out of the balloon.

Figure 5:
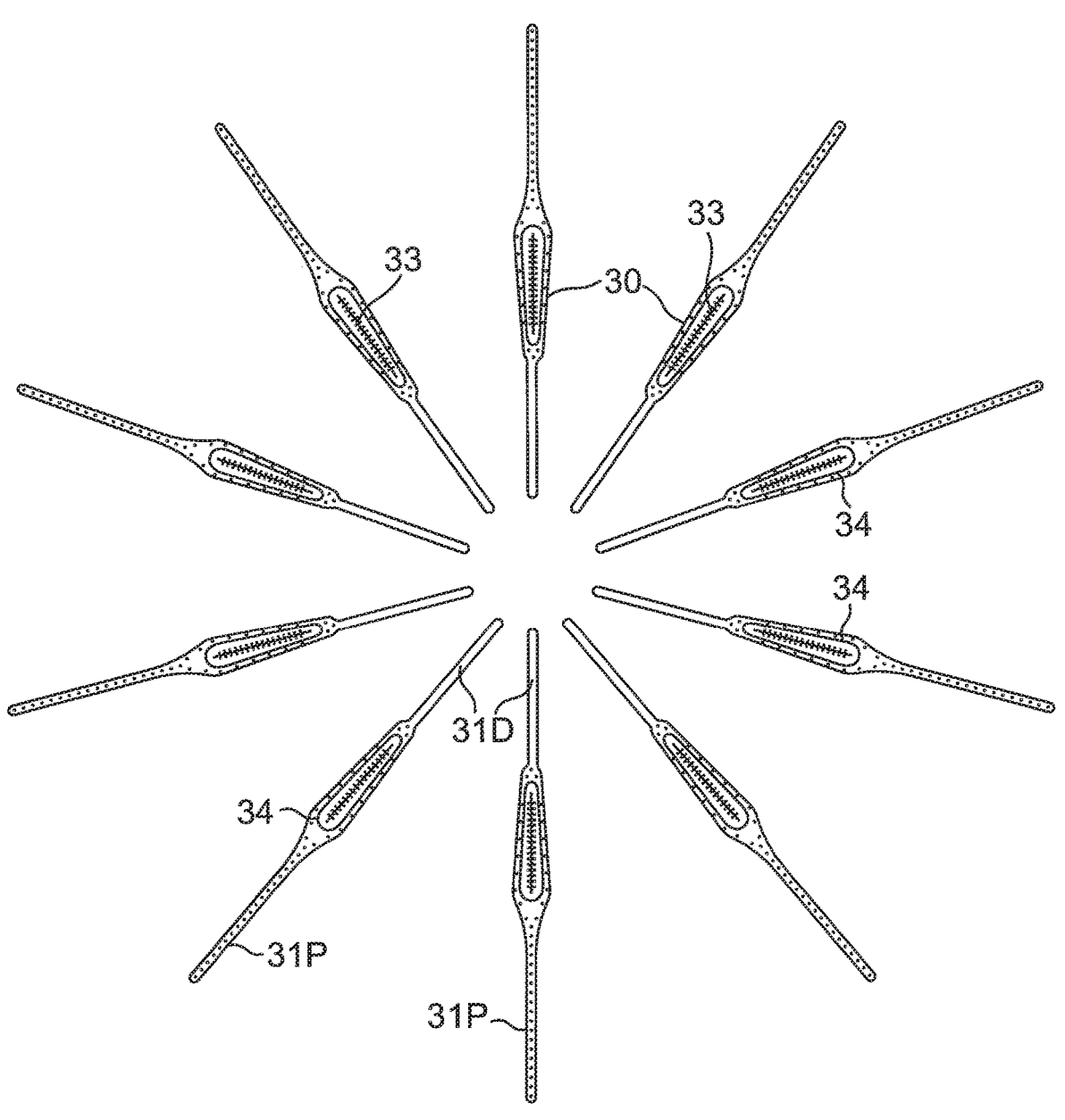
FIG. 5 is a top plan view of a plurality of flex circuit electrode assemblies, according to an embodiment of the present invention.

The membrane 26 supports and carries a combined electrode and temperature sensing member which is constructed as a multi-layer flexible circuit electrode assembly 84. The "flex circuit electrode assembly" 84 may have many different geometric configurations. In the illustrated embodiment, the flex circuit electrode assembly 84 has a plurality of radiating leaves or strips 30, as best seen in FIG. 5. The leaves 30 are evenly distributed about the distal end 88 and the balloon 80. Each leaf has wider proximal portion that gradually tapers to a narrower distal portion.

With reference to FIG. 3 and FIG. 5, each leaf 30 has a proximal tail 31P and a distal tail 31D. The proximal tail 31P is tucked under and fastened to the catheter 24 by a proximal ring 28P mounted on the proximal shaft portion 82 of the shaft 70. The distal tail 31D is tucked under and fastened to the catheter 24 by a distal ring (not shown). Either or both sets of tails 31D and 31P may be further covered by a respective semispherical cap, such as distal cap 28D. One or more contact electrodes 33 on each leaf come into galvanic contract with the ostium 11 during an ablation procedure, during which electrical current flows from the contact electrodes 33 to the ostium 11, as shown in FIG. 4.

Figure 6:
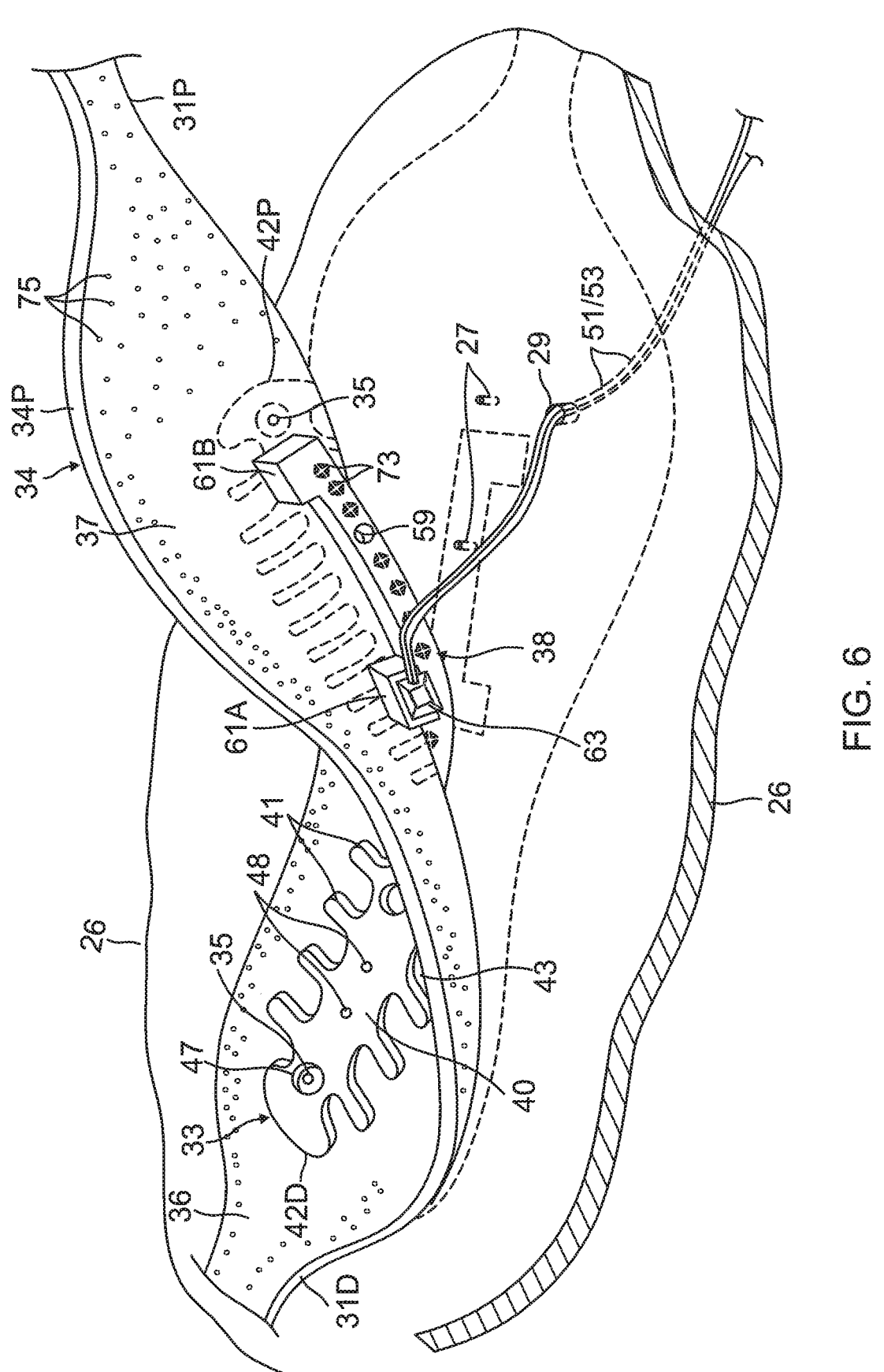
FIG. 6 is a perspective view of a flex circuit electrode assembly, accordingly to an embodiment of the present invention, partially lifted from the balloon.

For simplicity, the flex circuit electrode assembly 84 is described with respect to one of its leaf 30 as shown in FIG. 6, although it is understood that following description may apply to each leaf of the assembly. The flex circuit electrode assembly 84 includes a flexible and resilient sheet substrate 34, constructed of a suitable bio-compatible materials, for example, polyimide. In some embodiments, the sheet substrate 34 has a greater heat resistance (or a higher melting temperature) compared to that of the balloon membrane 26. In some embodiments, the substrate 34 is constructed of a thermoset material having a decomposition temperature that is higher than the melting temperature of the balloon membrane 26 by approximately 100 C or more.

The substrate 34 is formed with one or more irrigation pores or apertures 35 that are in alignment with the irrigation apertures 35 of the balloon member 26 so that fluid passing through the irrigation apertures 35 can pass to the ablation site on the ostium.

The substrate 34 has a first or outer surface 36 facing away from the balloon membrane 26, and a second or inner surface 37 facing the balloon membrane 26. On its outer surface 36, the substrate 34 supports and carries the contact electrodes 33 adapted for tissue contact with the ostium. On its inner surface 37, the substrate 34 supports and carries a wiring electrode 38. The contact electrode 33 delivers RF energy to the ostium during ablation and/or is connected to a thermocouple junction for temperature sensing of the ostium. In the illustrated embodiment, the contact electrode 33 has a longitudinally elongated portion 40 and a plurality of thin transversal linear portions or fingers 41 extending generally perpendicularly from each lateral side of the elongated portion 40 between enlarged proximal and distal ends 42P and 42D, generally evenly spaced therebetween. The elongated portion 40 has a greater width and each of the fingers has a generally uniform lesser width. Accordingly, the configuration or trace of the contact electrode 33 resembles a "fishbone." In contrast to an area or "patch" ablation electrode, the fingers 41 of the contact electrode 33 advantageously increase the circumferential or equatorial contact surface of the contact electrode 33 with the ostium while void regions 43 between adjacent fingers 41 advantageously allow the balloon 80 to collapse inwardly and/or expand radially as needed at locations along its equator. In the illustrated embodiment, the fingers 41 have different lengths, some being longer, others being shorter For example, the plurality of fingers include a distal finger, a proximal finger and fingers therebetween, where each of the fingers in between has a shorter adjacent finger. For example, each finger has a length different from its distal and/or proximal immediately adjacent neighboring finger(s) such that the length of each finger generally follows the tapered configuration of each leaf 30. In the illustrated embodiment, there are 22 fingers extending across (past each lateral side of) the elongated portion 40, with the longest finger being the third finger from the enlarged proximal end 42P. In some embodiments, the contact electrode 33 includes gold 58B with a seed layer 45, between the gold 58B and the membrane 26 (see FIG. 12A and FIG. 12B). The seed layer may include titanium, tungsten, palladium, silver, and/or combinations thereof.

Formed within the contact electrode 33 are one or more exclusion zone 47, each surrounding an irrigation aperture 27 formed in the substrate 26. The exclusion zones 47 are voids purposefully formed in the contact electrode 33, as explained in detail further below, so as to avoid damage to the contact electrode 33 during construction of the electrode assembly 84 in accommodating the irrigation apertures 27 at their locations and in their function.

Also formed in the contact electrode 33 are one or more conductive blind vias 48 which are conductive or metallic formations that extend through through-holes 55, as shown in FIG. 8A, in the substrate 34 and are configured as electrical conduits connecting the contact electrode 33 on the outer surface 36 and the wiring electrode 38 on the inner surface 37. It is understood that "conductive" is used herein interchangeably with "metallic" in all relevant instances.

In the illustrated embodiment, the contact electrode 33 measures longitudinally between about 0.1 inch and 1.0 inch, and preferably between about 0.5 inch and 0.7 inch, and more preferably about 0.57 inch, and has four exclusion zones 47 and nine blind vias 48.

On the inner surface 37 of the substrate 34, the wiring electrode 38 is generally configured as an elongated body generally similar in shape and size to the elongated portion 40 of the contact electrode 33. The wiring electrode 38 loosely resembles a "spine" and also functions as a spine in terms of providing a predetermined degree of longitudinal rigidity to each leaf 30 of the electrode assembly 84. The wiring electrode 38 is positioned such that each of the blind vias 48 is in conductive contact with both the contact electrode 33 and the wiring electrode 38. In the illustrated embodiment, the two electrodes 33 and 38 are in longitudinal alignment with other, with all nine blind vias 48 in conductive contact with both electrodes 33 and 38. In some embodiments, the wiring electrode 38 has an inner portion of copper 57 and an outer portion of gold 58.

Figure 14:
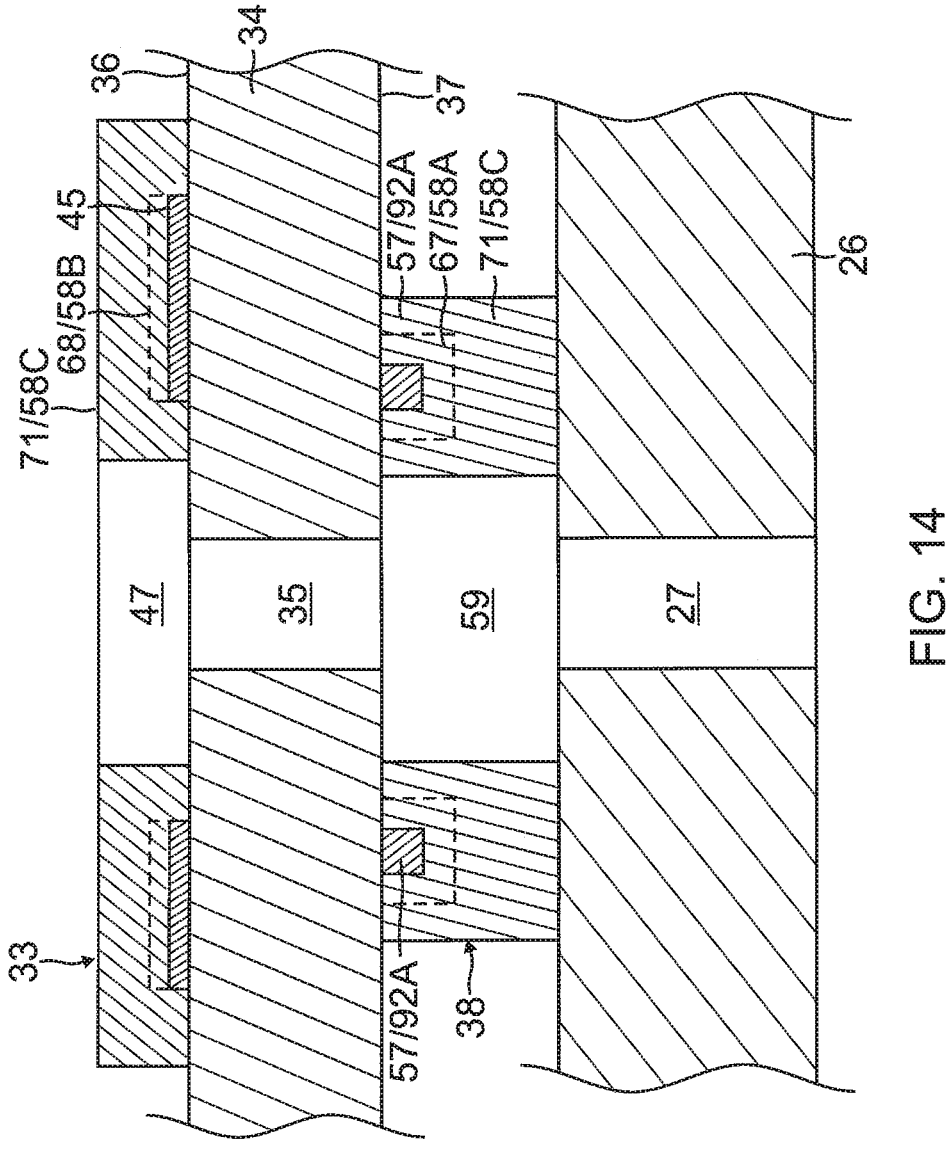

The wiring electrode 38 is also formed with its exclusion zones 59 around the irrigation apertures 35 in the substrate The flex circuit electrode assembly 84, including the leaves 30 and the tails 31P and 31D, is affixed to the balloon membrane 26 such that the outer surface 36 of the substrate 34 is exposed and the inner surface 37 of the substrate 34 is affixed to the balloon membrane 26, with the wiring electrode 38 and wire pair 51/53 sandwiched between the substrate 34 and the balloon membrane 26. The irrigation apertures 35 in the substrate 34 are aligned with the irrigation apertures 27 in the balloon membrane 26. The exclusion zones 59 in the wiring electrode 38 and the exclusion zones 47 in the contact electrode 33 are concentrically aligned with each other, as well as with the irrigation apertures 27 and 35, as shown in FIG. 14.

Methods of Construction

The present invention includes methods of constructing the flex circuit electrode assembly, and a balloon with the flex circuit electrode assembly. In some embodiments, the methods include the following Actions 1-9. It is understood that the Actions need not be taken in the sequence shown below, as desired or appropriate.

| | Actions |
|---|---|
| 1 | In forming a flex circuit electrode assembly, providing a flex circuit having a substrate, a first conductive layer and a second conductive layer. |
| 2 | Removing the first conductive layer to expose a first surface of the substrate. |
| 3 | Forming the wiring electrode in the second conductive layer; the forming may include forming an exclusion zone, active solder pad, and/or inactive solder pad. |
| 4 | Forming through-holes in the substrate to provide one or more blind vias and one or more irrigation apertures, the through-holes for forming the irrigation apertures to be in alignment with one or exclusion zones formed in the wiring electrode. |
| 5 | Applying a first added conductive layer on all exposed conductive surfaces. |
| 6 | Forming the contact electrode on first surface of the substrate; the forming may include using a photoresist and application of a seed layer and a second added conductive layer; the forming may include forming one or more exclusion zones in alignment with the irrigation apertures of the substrate. |
| 7 | Applying another additional conductive layer on all exposed conductive surfaces on the substrate, the wiring electrode and the contact electrode to form a flex circuit electrode assembly. |
| 8 | Preparing flex circuit electrode assembly for affixation; the preparing may include attaching wire pair to an active solder pad and/or perforating peripheral regions of substrate. |
| 9 | Affixing the flex circuit electrode assembly to an outer surface of a balloon member. |

34. The wiring electrode 38 is further formed with solder pad portions 61, at least one active 61A, and there may be one or more inactive solder pad portions 61B. The solder pad portions 61A and 61B are extensions from a lateral side of the elongated body of the wiring electrode 38. In the illustrated embodiment, an active solder pad portion 61A is formed at about a mid-location along the elongated body, and a respective inactive solder pad portion 61B is provided at each of the enlarged distal end 42D and the enlarged proximal end 42P.

Attached, e.g., by a solder weld 63, to the active solder pad portion 61A are the wire pair, e.g., a constantan wire 51 and a copper wire 53. The copper wire 53 provides a lead wire to the wiring electrode 33, and the copper wire 53 and the constantan wire 51 provide a thermocouple whose junction is at solder weld 63. The wire pair 51/53 are passed through a through-hole 29 formed in the membrane 26. It is understood that, in other embodiments in the absence of the through-hole 29, the wire pair 51/53 may run between the membrane 26 and the substrate 34 and further proximally between the membrane 26 and the proximal tail 31P until the wire pair 51/53 enters the tubular shaft 70 via another through-hole (not shown) formed in the tubular shaft sidewall closer to the proximal ring 28.

The Actions 1-9 are discussed in more detail below, with reference to FIGS. 7-13, in conjunction with FIG. 6.

1) Providing a flex circuit 90 having a flexible substrate 34 whose first or outer surface 36 is generally covered with a first conductive layer 91 and whose second or inner surface 37 is generally covered with a second conductive layer 92, as shown in FIG. 7. In some embodiments, the substrate 34 is constructed of polyimide and the first and second conductive layers 91 and 92 are copper.

2) Removing the first conductive layer 91, as shown in FIG. 8A and FIG. 8B. In some embodiment, the first conductive layer 91 of copper is removed from the outer surface 36 of the substrate 34 by chemical etching to expose the outer surface of the substrate.

3) Forming the wiring electrode 38 in the second conductive layer 92, as shown in FIGS. 8A and 8B. Forming the wiring electrode 38 may include forming the elongated body with at least an exclusion zone 59. Forming the wiring electrode 38 may include forming at least one active solder pad 61A. Forming the wiring electrode 38 may include forming at least one inactive solder pad 61B capable of functioning as a visual radiopaque marker. In some embodiments, forming the wiring electrode 38 includes masking a configuration of the elongated body in a first portion 92A of the second conductive layer 92, with one or more solder pads, while leaving unmasked a second portion 92B and one or more exclusion zones 59 in the first portion 92A; and removing the second conductive layer 92B in the unmasked one or more exclusion zones 59 and the second portion 92B from the inner surface 37 of the substrate 34 by chemical etching.

Figures 9A, 9B:
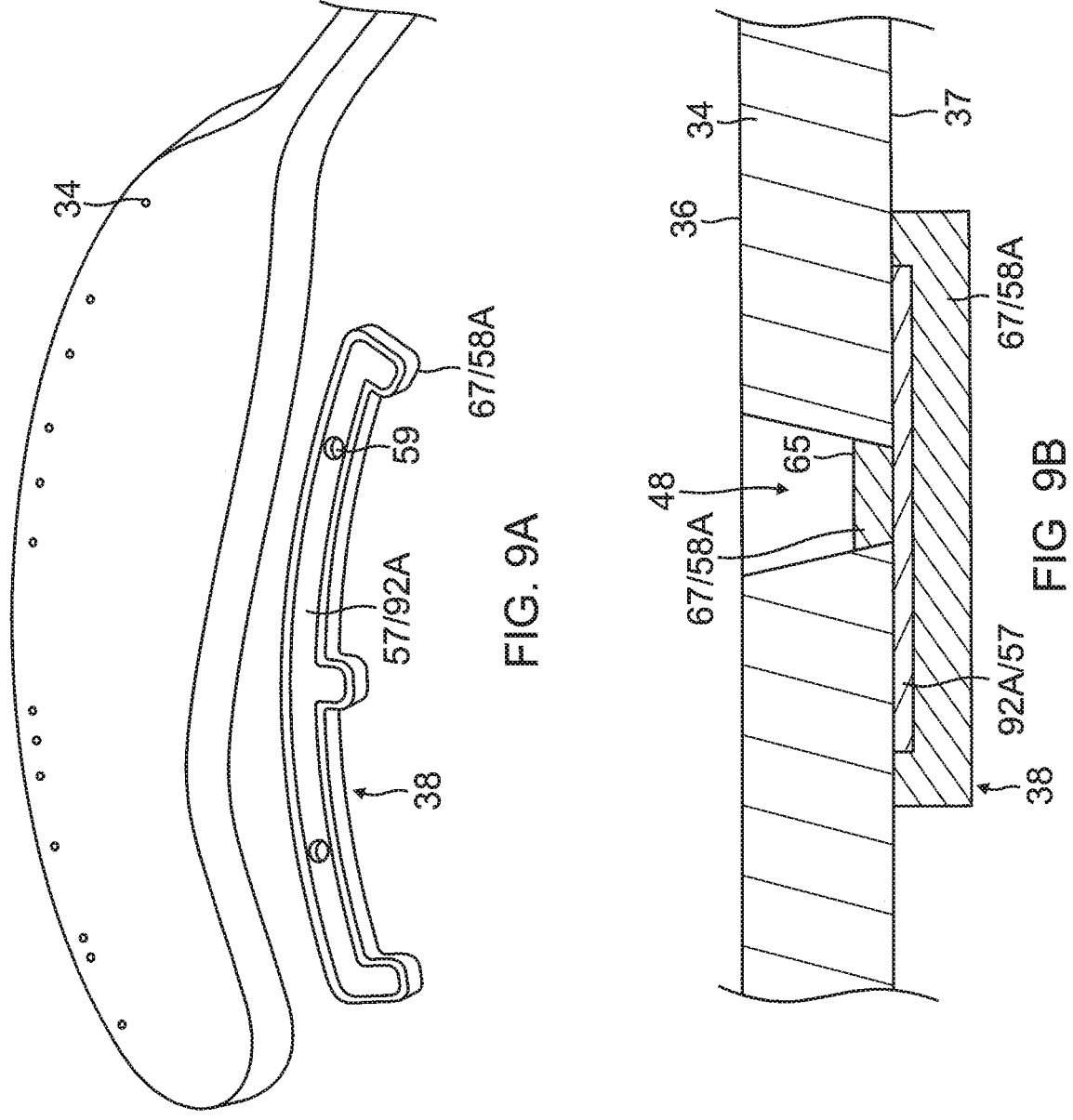

4) Forming one or more through-holes 55 in the substrate 34 to provide one or more blind vias 48 and forming one or more irrigation apertures 35, as shown in FIG. 8A and FIG. 9A. In some embodiments, forming a through-hole 55 and/or the irrigation aperture 35 includes laser drilling through the substrate 34 from a direction facing the outer surface 36, at location within a perimeter trace 66 (shown in broken lines in FIG. 10) of the contact electrode 33 and to a depth through the entire thickness of substrate 34. In forming the through-hole 55 for the blind via 48, the laser drilling is performed generally without penetrating the wiring electrode 38.

5) Applying an added conductive layer 67 on all exposed conductive surfaces on the substrate 34 and wiring electrode 38, as shown in FIG. 9A and FIG. 9B. In some embodiments, the substrate 34 with the wiring electrode 38 being formed is immersed in a gold plating bath to form a gold layer 58A covering exposed conductive surfaces of the elongated body of the wiring electrode 38 and a bottom surface 65 of any and all blind vias 48.

Figure 10:
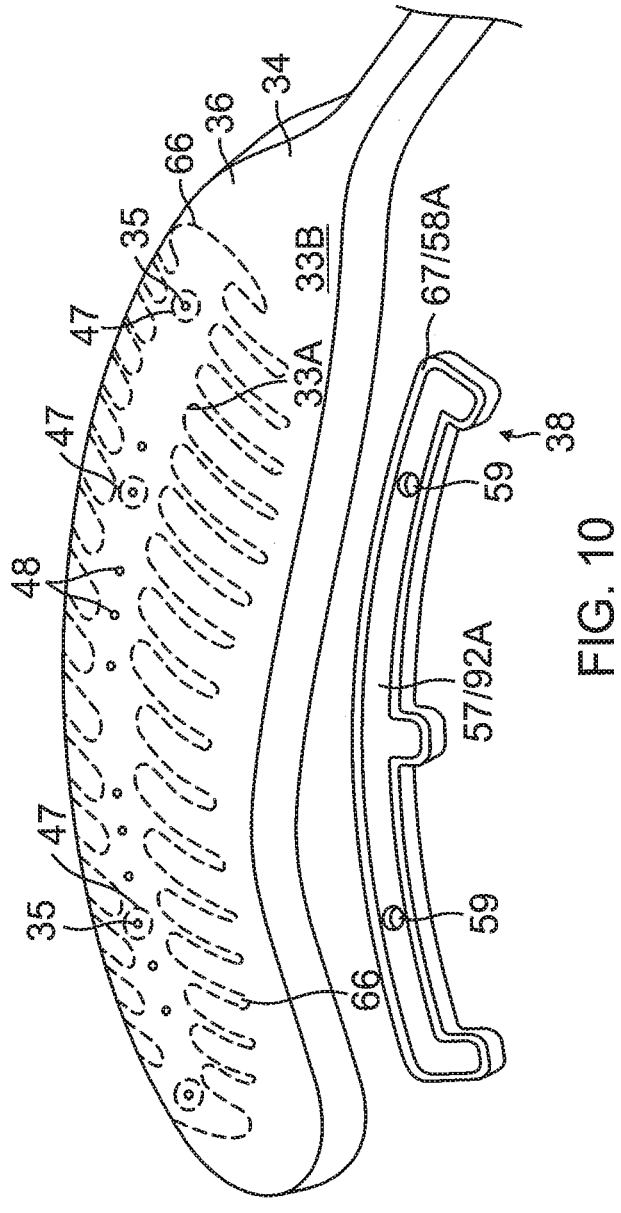
Figure 11A:
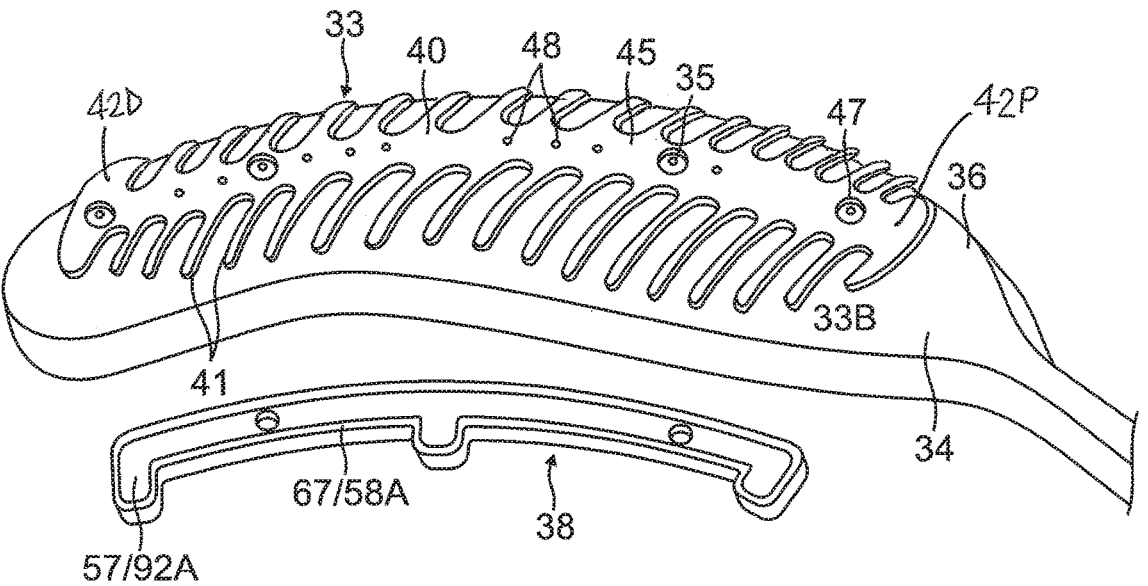
Figure 11B:
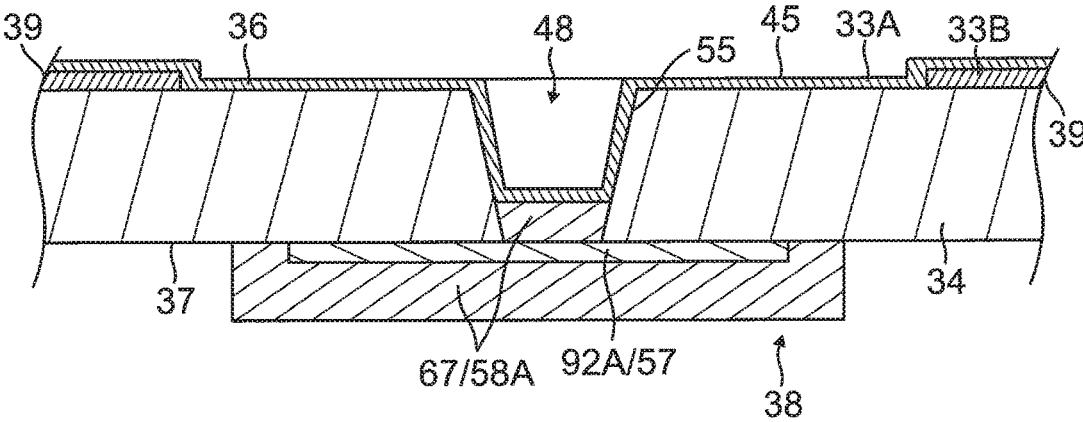
Figure 12A:
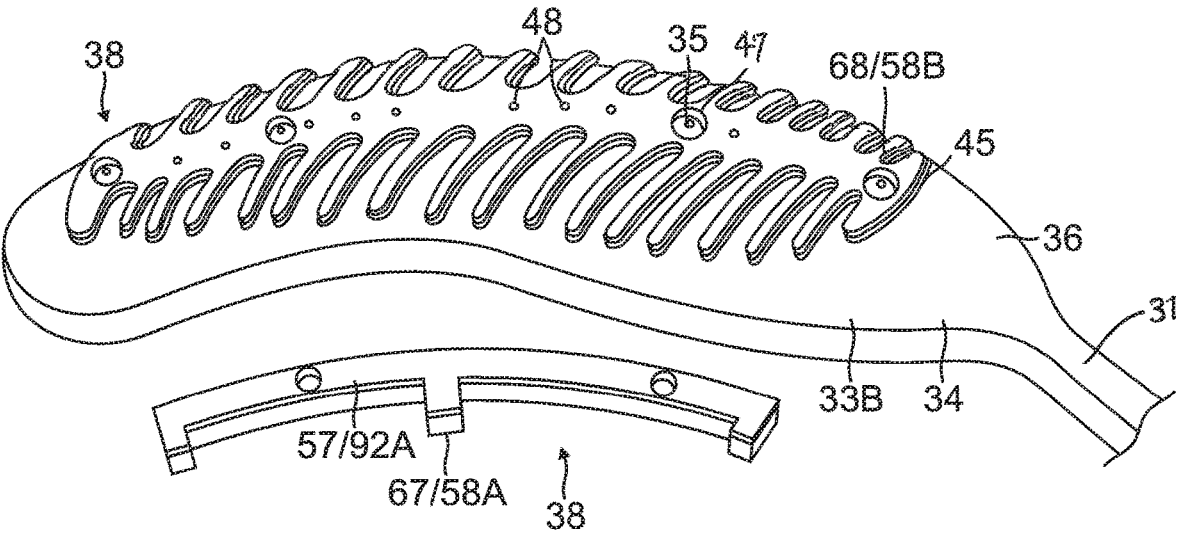
Figure 12B:
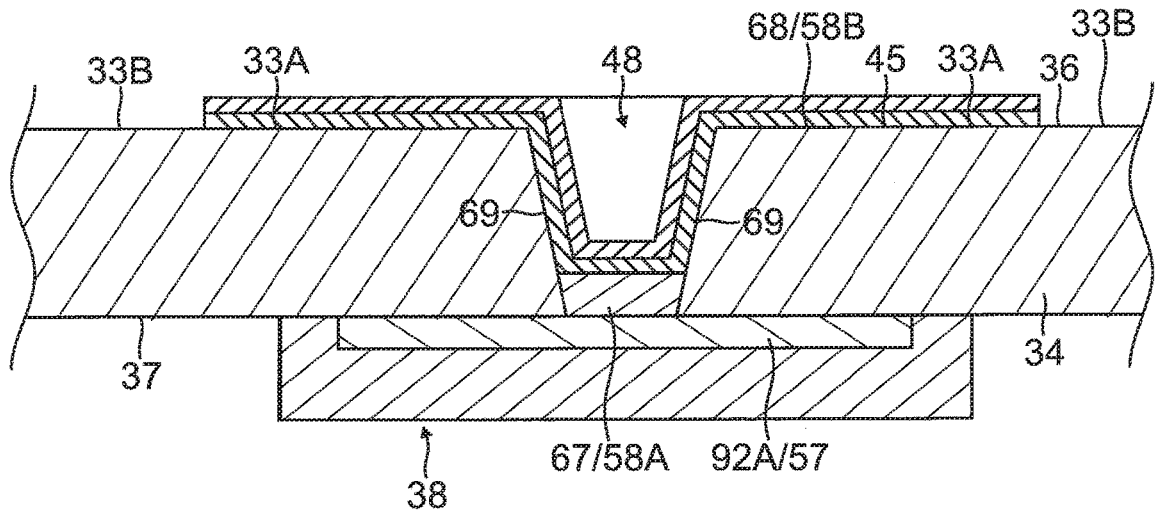

6) Forming the contact electrode 33 on the exposed outer layer 36 of the substrate 34, as shown in FIG. 10, FIG. 11A, FIG. 12A and FIG. 13. In some embodiments, forming the contact electrode 33 includes (i) defining a first region 33A within a perimeter trace 66 in a configuration of the fishbone (including the elongated body 40 and the fingers 41) on the outer surface 36 of the substrate 34, as shown in FIG. 10, (ii) applying photoresist 39 to a second region 33B outside of the first region 33A on the outer layer 36 of the substrate 34, as shown in FIG. 11B, (iii) applying a seed layer 45 onto the outer surface 36 of the substrate 34 in at least the first region 33A, as shown in FIG. 11A and FIG. 11B, (iv) applying another added conductive layer 68, e.g., gold 58B, on at least the seed layer 45, as shown in FIG. 12A and FIG. 12B, and (v) removing the photoresist 39 from the substrate 34 along with any portions of the seed layer 45 and the conductive layer 68 on the photoresist 39, as shown in FIG. 12A and FIG. 12B. In some embodiments, applying photoresist 39 includes applying photoresist 39 to one or more exclusion zones 47 in the elongated portion 40 of the contact electrode 33 surrounding an irrigation aperture 35 formed in the substrate 34. In some embodiments, applying a seed layer 45 includes sputtering the seed layer 45 to inside the one or more blind vias 48. In some embodiments, applying the conductive layer 68 includes sputtering the conductive layer 68 to inside the one or more blind vias 48. In some embodiments, the blind vias are formed with sloping or tapered sidewalls 69 (see FIG. 12B) which are covered with the seed layer 45 and the conductive layer 68/58B.

Figure 13A:
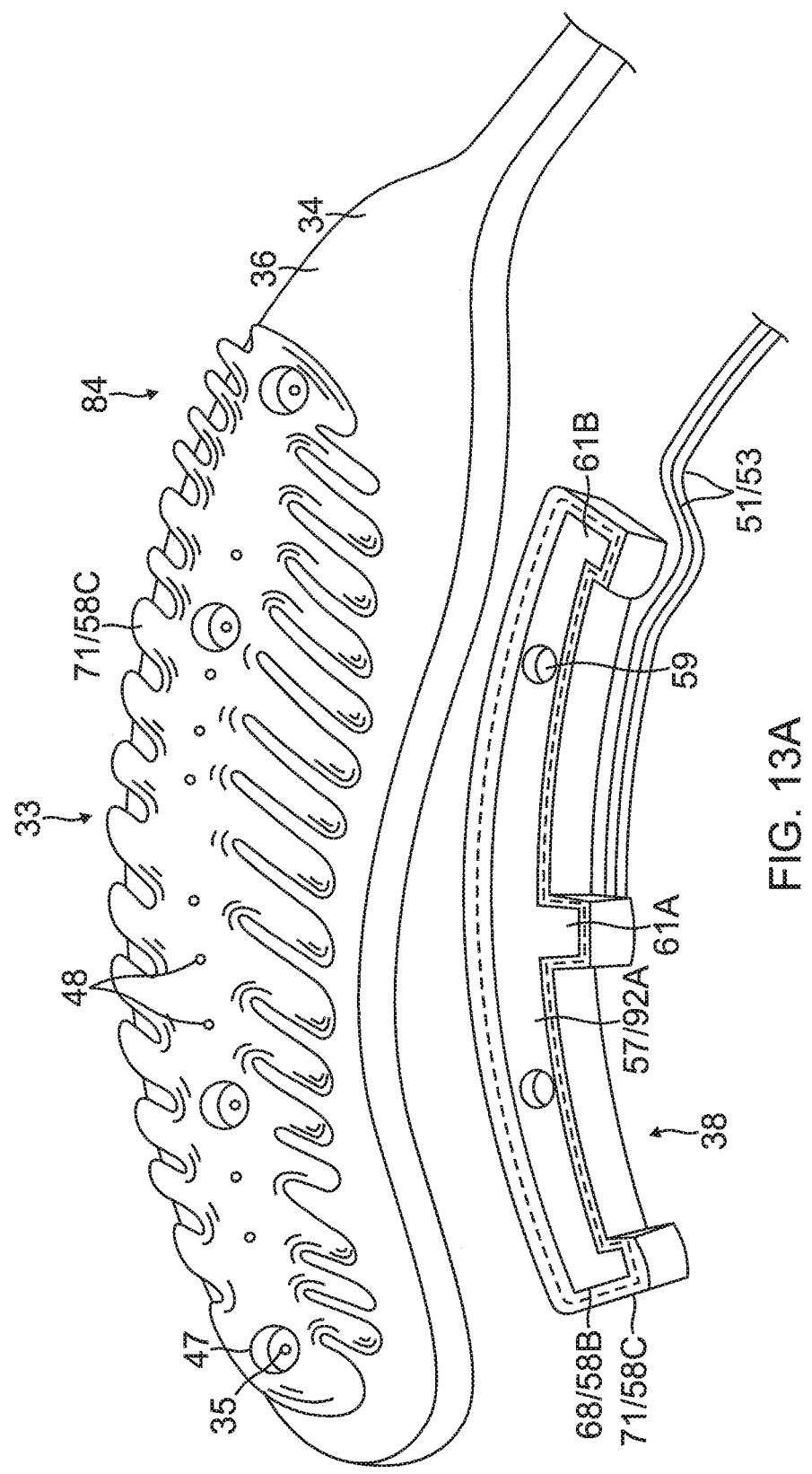
Figure 13B:
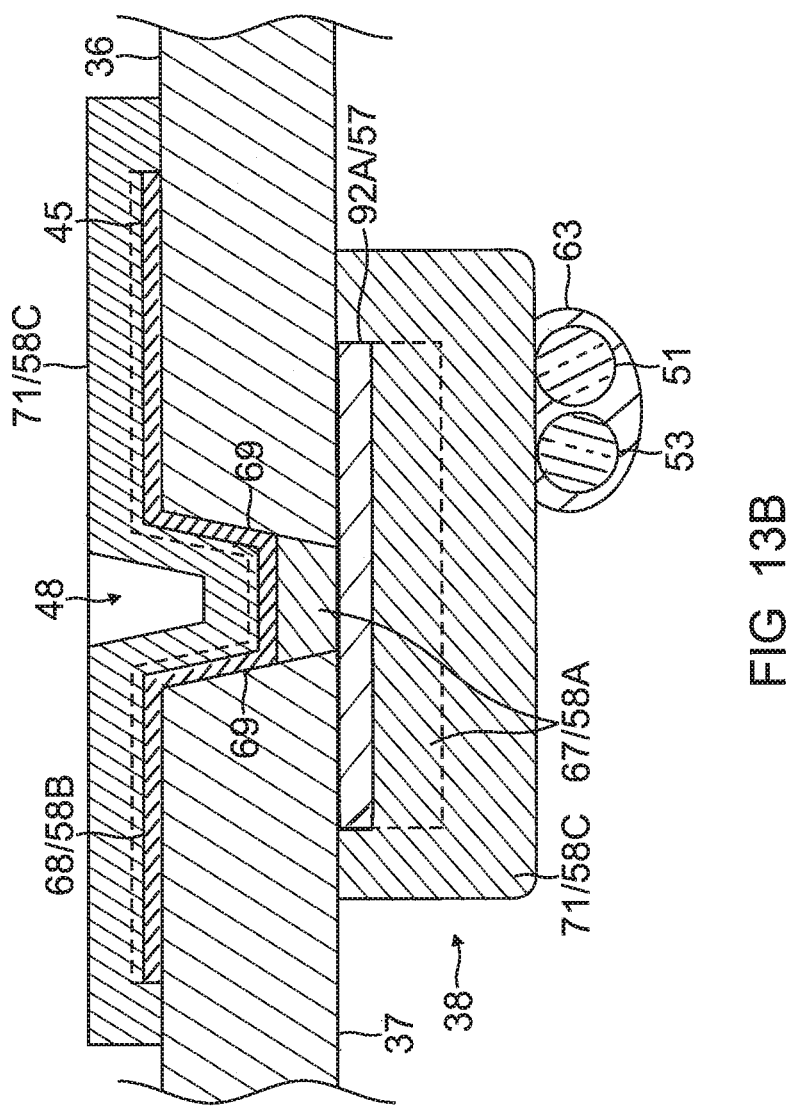

7) Applying yet another conductive layer 71 on all exposed conductive surfaces on the substrate 34, including the contact and wiring electrodes 33 and 38, as shown in FIG. 13A and FIG. 13B. In some embodiments, the substrate 34 inclusive of the electrodes 33 and 38 is immersed again in a gold plating bath to form another gold layer 58C covering exposed conductive surfaces of the electrode 33 and 38 and all blind vias 48. In some embodiments, radiopaque markers 73 are applied or painted onto the gold layer 58C covering the wiring electrode 38. For example, a mixture comprising tungsten and epoxy can be painted onto the gold layer 58C on the wiring electrode 38 to serve as radiopaque markers.

8) Preparing the flex circuit electrode assembly 84 for affixation to the balloon 80, as shown in FIG. 6. The Actions 1-7 described above form the electrodes 33 and 38 on the substrate 34 in forming a flex circuit electrode assembly 84 which may then be prepared for affixation to a balloon membrane 26. In some embodiments, the wire pair 51/53 are soldered to the active solder pad 61A, wherein the wire pair 51/53 function as a thermocouple, and the copper wire 53 functions as a lead wire delivering RF energy to the wiring electrode 38 which in turn energizes the contact electrode 33. In some embodiments, peripheral regions 34P of the substrate 34 are formed with a plurality of perforations 75 configured to receive an adhesive for affixing the electrode assembly 84 to the balloon membrane 26.

9) Affixing the flex circuit electrode assembly 84 to the balloon membrane 26, as shown FIG. 6. In some embodiments, the wire pair 51/53 are fed through a through-hole 29 formed in the membrane 26 of and an adhesive (not shown) is applied to generally the entire inner surface 37 of the substrate 34, inclusive of the wiring electrode 38, to adhere the flex circuit electrode assembly 84 to the membrane 26.

It is understood that the present invention includes other embodiments with more simplified actions and/or less actions than those described above. For example, forming the contact electrode in the configuration of a "fishbone" may include sputtering the seed layer and the second added conductive layer directly on the balloon membrane, thus eliminating the use of a substrate and a wiring electrode. Appropriate wiring may be provided in the configurations described herein and/or with similar blind vias, full vias (i.e., that pass through the contact electrode, the substrate, the wiring electrode, the contact microelectrode, and/or the wiring microelectrode), conductive traces, etc., as understood by one of ordinary skill in the art. Such a balloon catheter would nonetheless offer all the advantages afforded by a "fishbone" contact electrode, as described herein.

Figure 15A:
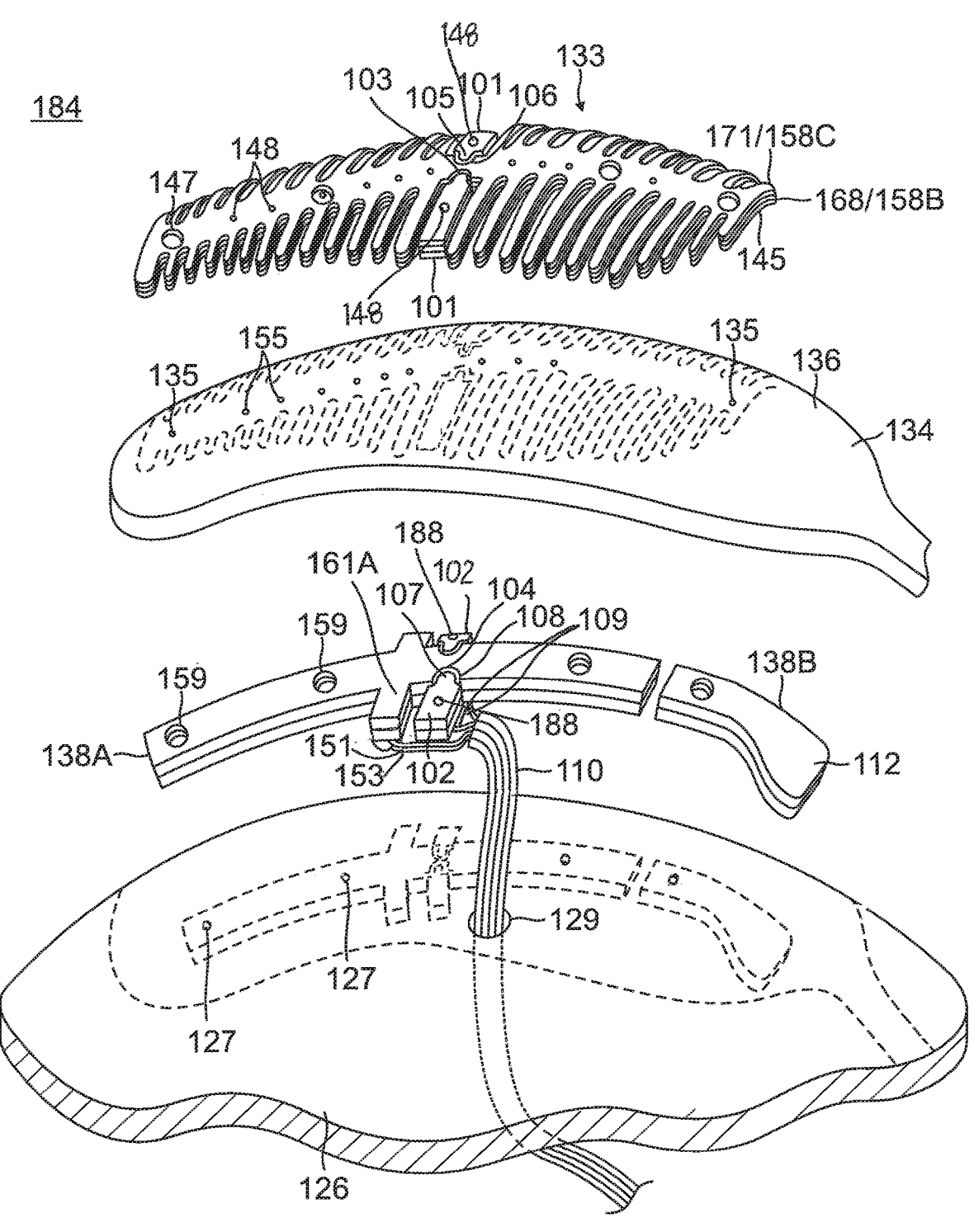
FIG. 15A is an exploded perspective view of a flexible circuit electrode assembly, according to another embodiment of the present invention, with parts of the contact electrode broken away to show its layers.

In other embodiments of the present invention, a flex circuit electrode assembly 184, as shown in FIG. 15A, includes one or more contact microelectrodes 101 and wiring microelectrodes 102 physically and electrically isolated from contact electrode 133 and wiring electrode 138, respectively. Pairs of aligned contact microelectrode 101 and wiring electrode 102 are conductively connected to each other by a blind via 148. The one or more microelectrodes 101 and 102 are formed concurrently with the formation of the respective electrode 133 and 138 per the aforementioned Actions. In the illustrated embodiment, the microelectrodes 101 and 102 are positioned near a midpoint along the length of the electrodes 133 and 138, so that the microelectrodes 101 and 102 are near the equatorial region of the balloon 80, although it is understood that they may be located at other locations relative to the electrodes 133 and 138. The microelectrodes 101 and 103 are configured for impedance, electrical signals, and/or temperature sensing independently of the electrodes 133 and 138 and thus are physically and electrically isolated from the contact electrode 133 and the wiring electrode 138, respectively by one or more respective exclusion zones 103 and 104.

Figure 15B:
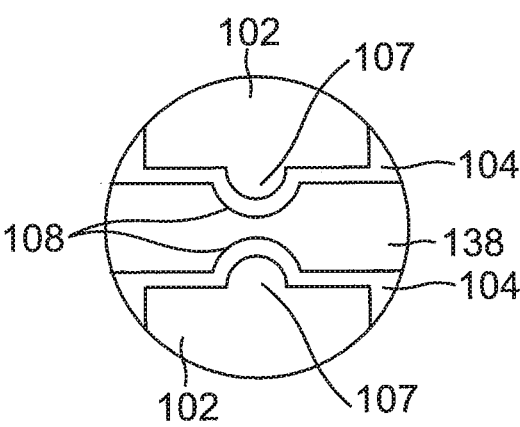
FIG. 15B is a detailed top plan view of a wiring microelectrode separated from a wiring electrode by an exclusion zone, according to an embodiment of the present invention.

For forming the wiring microelectrodes 102, for example, photoresist is applied to outer surface 136 of substrate 134 where the exclusion zones 103 are to be formed. In the illustrated embodiment, as shown in FIG. 15B, the wiring microelectrodes 102 are formed with protrusions 107 that project into conforming recesses 108 formed in elongated body of the wiring electrode 138. Spanning between the protrusions 107 and the recesses 108, the exclusion zones 104 adopt a conforming configuration between the wiring electrode 138 and the wiring microelectrode 102.

Figure 15C:
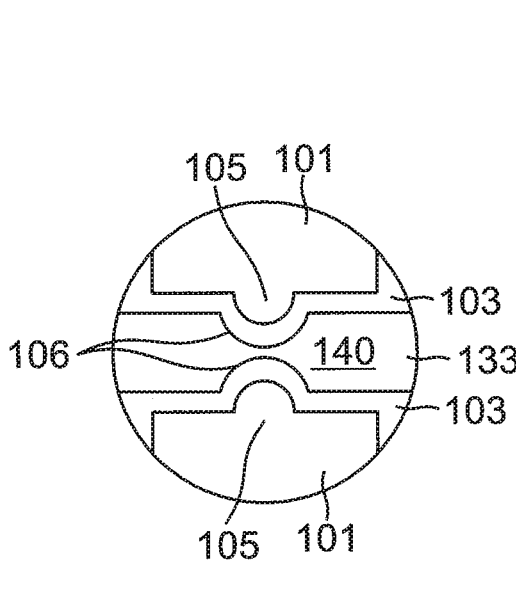
FIG. 15C is a detailed top plan view of a contact micro-electrode separated from a contact electrode by an exclusion zone, according to an embodiment of the present invention.

For the contact microelectrodes 101, they are formed by appropriately masking a second conductive layer 192 (not shown) on inner surface 137 of the substrate 134 in the configuration of the contact microelectrodes 101. In the illustrated embodiment, as shown in FIG. 15C, the contact microelectrodes 101 are masked with protrusions 105 projecting into recesses 106 formed in elongated portion 140 of the contact electrode 133. Spanning between the protrusions 105 and the recesses 106, the exclusion zones 103 adopt a conforming configuration between the contact electrode 133 and the electrode 133 and the contact microelectrode 101.

The protrusions 105 and 107 allow the microelectrodes 101 and 102 to be as close as possible to the contact and wiring electrodes 133 and 138 and hence as close as possible to the tissue contact site, while maintaining physical and electrical isolation, Wire pair 151/153 are soldered to active solder pad 161A. A lead wire (e.g., copper wires) 109 is soldered to a respective wiring microelectrode 102. The wires 151, 153 and 109 are part of a ribbon cable 110 that extends through through-hole 129 formed in balloon membrane 126.

The wiring electrode 138 is shown as a "split" electrode comprising a first or distal elongated portion 138A and a second or proximal elongated portion 138B. The second wiring electrode portion 138B may function as a radiopaque marker with an enlarged portion 112 on one lateral side as a visual indicator under fluoroscopy of, for example, a specific wiring electrode, such as a "first" wiring electrode, and/or a direction toward subsequently numbered wiring electrodes around the circumference of balloon 180. The second wiring electrode portion 138B may also be active where respective lead wires are connected thereto to deliver RF energy to it. In the latter regard, however, it is understood that in some embodiments a plurality of active wiring electrodes (or active split wiring electrode portions) may each have its own copper wire while sharing a common constantan wire. In any instance, such wire pairs may provide both RF energizing functions and temperature sensing functions.

Figure 17:
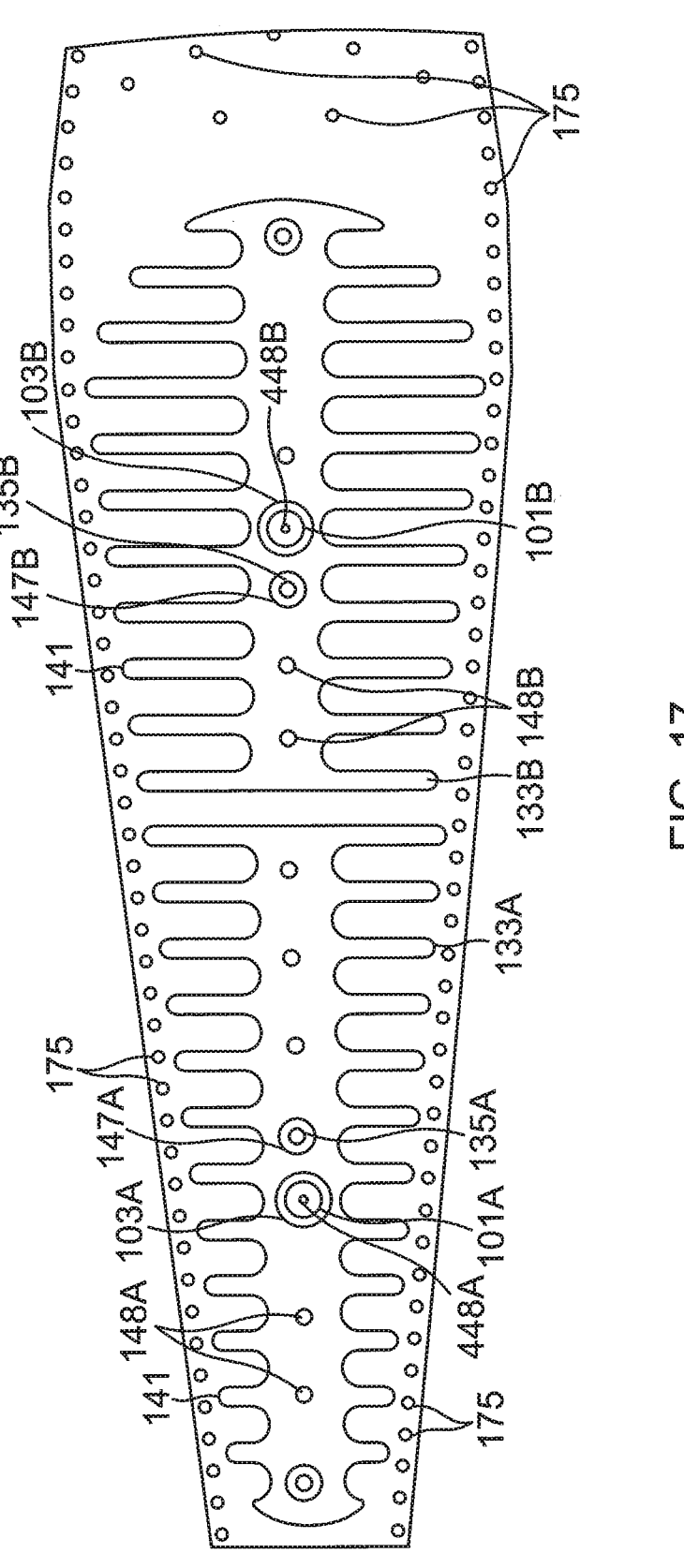
FIG. 17 is a top plan view of a flex circuit electrode assembly with a split contact electrode, according to an embodiment of the present invention.

As for the contact electrode 133, it may also be split into contact electrode portions 133A and 1338, as shown in FIG. 17, in correspondence with the split wiring electrode portions 138A and 1388, where the contact electrode portion 133A is conductively connected by blind vias 148A to the wiring electrode portion 138A, and contact electrode portion 133B is conductively connected by blind vias 148B to wiring electrode portion 138B.

Figure 16A:
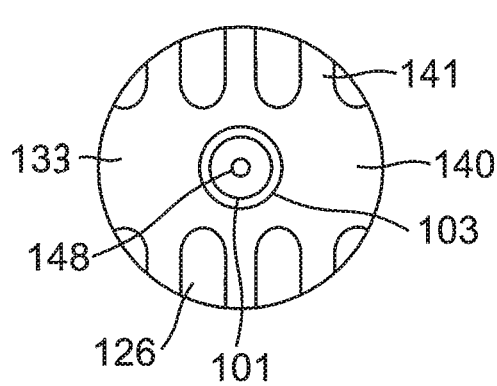
FIG. 16A is a detailed top plan view of an "island" contact microelectrode located in a contact electrode, according to an embodiment of the present invention.
Figure 16B:
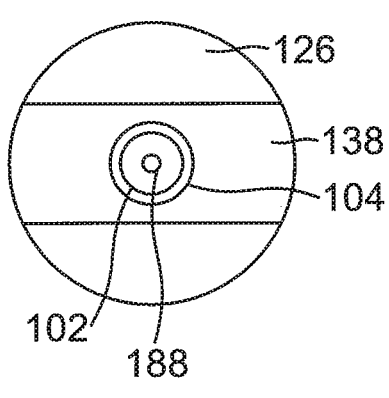
FIG. 16B is a detailed top plan view of an "island" contact microelectrode located in a contact electrode, according to an embodiment of the present invention.

It is understood that microelectrodes 101 and 102 may also be formed as "islands" (of any suitable shape and size), each surrounded in its entirety by the exclusion zones 106 and 107, respectively, formed in the electrodes 133 and 138 (in full, or in split electrode portions), respectively, as shown in FIG. 16A, FIG. 16B and FIG. 17. A blind via 148 may be formed in each contact microelectrode 101 to provide a conductive connection with its wiring microelectrode 102. A full via 188 may be formed in each wiring microelectrode 102 as a conductive connection to its wire pair, which can enable the microelectrodes 101 and 102 for ablation, electropotential, sensing, impedance detection and/or temperature sensing.

Figure 18A:
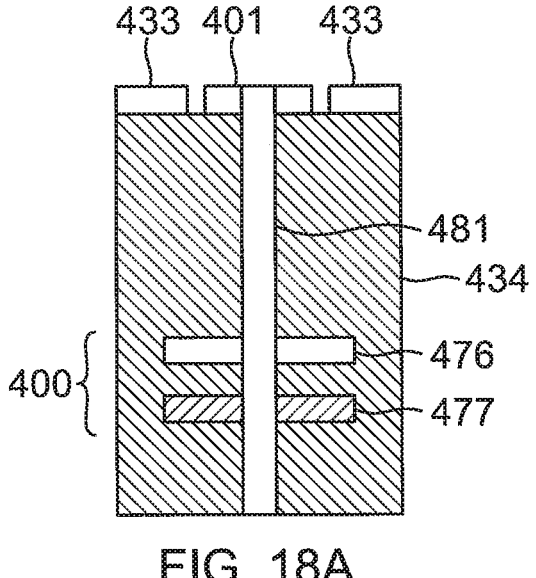
FIG. 18A is a side cross-sectional view of an embedded thermocouple, according to an embodiment of the present invention.

FIG. 18A illustrates a thermocouple 400 formed from a copper conductor or wire 476 connected to a constantan conductor or wire 477 by a conducting via 481. The wires 476 and 477 are formed as conducting lines embedded in substrate 424. The via 481 also connects to a contact microelectrode 401 on the outer surface of the substrate. By connecting the thermocouple 400 to the microelectrode 401, electropotential signals from tissue contacting the microelectrode 401 may be acquired while the temperature of the tissue is also measured. Alternatively, for instance in the case where contact electrode 433 is being used for ablation, the temperature of tissue contacting the microelectrode 401 may be measured without acquiring electropotential signals from the microelectrode 401.

Figure 18B:
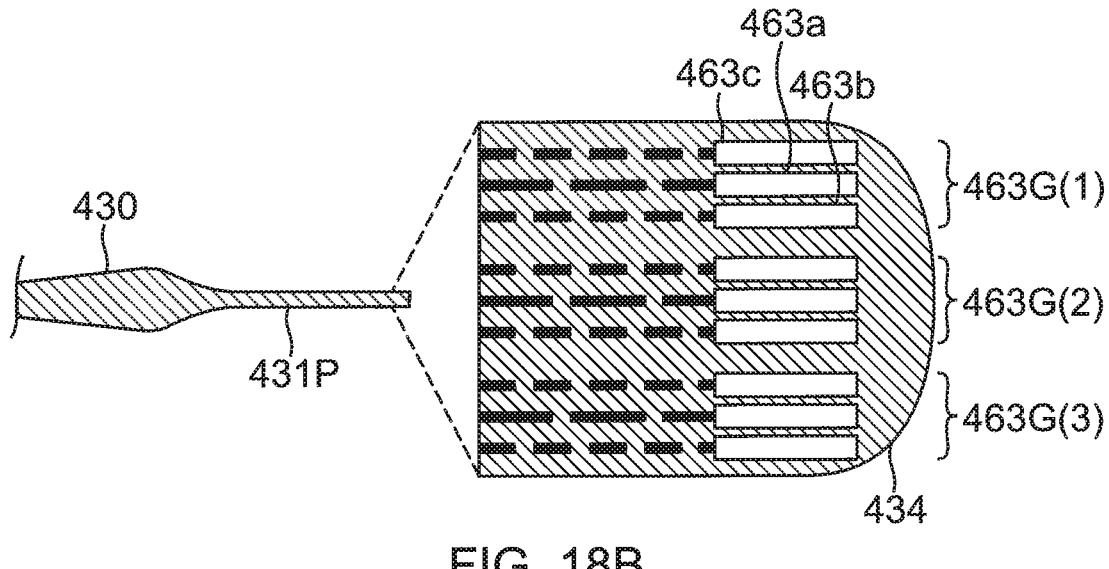
FIG. 18B is a top sectional view of an embedded solder pad sets, according to an embodiment of the present invention.

As shown in FIG. 18B, the wires 476 and 477 exit at solder pads 463a and 463b, respectively, which are located remotely from the microelectrode 401, in a region of the proximal tail 31P, for example, near its tip end. The potential between the solder pads 463a and 463b comprises a signal to the temperature module 52 in the console 15 (FIG. 1), and the module uses the signal to formulate the temperature measured by the thermocouple 400 at the location of the microelectrode 401. Moreover, the solder pad 463a connected to the copper wire 476 and/or the solder pad 463b connected to the constantan wire 477 may also be used to acquire electropotentials formed on the microelectrode 401 that the solder pad is connected to by via 481. The ECG module 56 of the console 15 (FIG. 1) typically receives signals derived from the solder pads 463a and/or 463b, and analyzes the signals to derive the electropotentials at the microelectrode 401.

A solder pad 463c is connected, via another conducting wire embedded in substrate 434, to contact electrode 433 and the solder pad 463c may be used to transfer electromagnetic RF ablation energy, generated by the ablation module 54 of the console 15 (FIG. 1), to the contact electrode 433. As shown in FIG. 18B, the solder pads 463c, 463a and 463b may be grouped as a set of three solder pads 463G(1) connecting to the contact electrode 433, the microelectrode 401 and the thermocouple 400. A set of three pads 463G(i) may be connected to a set of contact electrode, microelectrode and thermocouple. Notably, the location of at least the solder pads 463a and 463b can be advantageously remote from the location of where the temperature is measured, so that any bulkiness embodied in the solder pads 463a and 463b can be avoided at location of the microelectrode 401 where tissue contact occurs.

As shown in FIG. 15, irrigation apertures 127 are formed in the balloon membrane 126, irrigation apertures 135 are formed in the substrate 134, exclusion zones 147 are formed in the contact electrode 133, and exclusion zones 159 are formed in the wiring electrode 138.

In some embodiments, the substrate 34, 134 (e.g., polyimide) has a thickness of about 25.0 microns. The wiring electrode 38, 138 includes an inner layer of copper having a thickness of about 2.0 microns and an outer layer of gold of having a thickness of ranging between about 1.0 and 50 microns, and preferably between about 2.75 microns and 37 microns, where the thickness of the gold depends on how much radiopacity is desired or appropriate. The contact electrode 33, 133 includes a seed layer having a thickness of about 0.01-0.05 microns and an outer layer of gold having a thickness of about 1.0 micron. The balloon membrane 26, 126 may have an average thickness of about 25.0 microns as it understood that the membrane may have a nonuniform thickness due to the method of manufacture.

In operation, the wire pair 51/53 conduct RF energy provided by the ablation module 54 of the console 15 (FIG. 1) through the control handle and the catheter shaft to the wiring electrode 38 which in turn energizes the contact electrode 33 through the blind vias 48.

In some embodiments, where the balloon 80 includes a flex circuit electrode assembly with 10 leaves (providing 10 contact electrodes), 10 functionally satisfactory lesions can be generated by discharging 25 W of RF power through each of the contact electrode 33 simultaneously, i.e., for a total of 250 W, for ten seconds or less. By generating lesions using high power in short durations, effectively using a "pulse" of power, heat dissipation from the site being ablated is minimized. In other words, the short duration of ablation helps to concentrate the heat energy at the site, and less energy is transferred away from the site.

In other embodiments, suitable ranges of power supplied to each contact electrode include between about 15-25 W for 10 seconds and 10-20 W for 60 seconds. In other embodiments, the power supplied to each contact electrode is at 25 W or higher for ten seconds or less.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings are not necessarily to scale. Moreover, it is understood that the actions described above need to be taken in other sequences as desired or appropriate. Accordingly, the foregoing description should not be read as pertaining only to the precise structures described and illustrated in the accompanying drawings, but rather should be read consistent with and as support to the following claims which are to have their fullest and fair scope.

What is claimed is:

1. An electrophysiology catheter adapted for use in an ostium, comprising:
   a balloon having a membrane, the balloon having a distal end and a proximal end defining a longitudinal axis;
   a plurality of radiating strips disposed on the membrane, each of the plurality of radiating strips having a tapered configuration in which a wider proximal portion having a proximal end tapers to a narrower distal portion having a distal end; and
   a contact electrode supported on each of the plurality of radiating strips, the contact electrode including:
   an elongated portion, and
   a plurality of transversal fingers extending from the elongated portion, the plurality of transversal fingers comprising a first finger disposed adjacent to and in between a second finger and a third finger, the first finger being longer than the second finger and the third finger such that the plurality of transversal fingers follows the tapered configuration of each of the plurality of radiating strips.

2. The electrophysiology catheter of claim 1, in which a width of the elongated portion is greater than a width of the first finger.

3. The electrophysiology catheter of claim 1, in which the first finger is longer than any other of the plurality of transversal fingers and is situated closer to an equatorial region of the balloon than most of the plurality of transversal fingers.

4. The electrophysiology catheter of claim 3, in which two fingers of the plurality of transversal fingers are disposed between the first finger and the proximal end.

5. The electrophysiology catheter of claim 1, in which the plurality of transversal fingers each have a generally uniform width.

6. The electrophysiology catheter of claim 1, in which the contact electrode comprises gold.

7. The electrophysiology catheter of claim 6, in which the contact electrode comprises a seed layer below the gold.

8. An electrophysiology catheter, comprising:
   a balloon with a membrane; and
   a flex circuit electrode assembly on the membrane, including:
   a plurality of radiating strips disposed on the membrane, each of the plurality of radiating strips having a tapered configuration in which a wider proximal portion having a proximal end tapers to a narrower distal portion having a distal end, each of the plurality of radiating strips comprising a substrate having a first surface and a second surface;
   a contact electrode disposed on each first surface of the substrate of each of the plurality of radiating strips, the contact electrode including:
   an elongated portion, and
   a plurality of transversal fingers extending from the elongated portion, the plurality of transversal fingers comprising a first finger disposed adjacent to and in between a second finger and a third finger, the first finger being longer than the second finger and the third finger such that the plurality of transversal fingers follows the tapered configuration of each of the plurality of radiating strips;
   a wiring electrode disposed on each second surface of the substrate of each of the plurality of radiating strips; and
   a conductive via extending through the substrate of each of the plurality of radiating strips and connected to the contact electrode and the wiring electrode.

9. The electrophysiology catheter of claim 8, in which the substrate includes a first irrigation aperture and the membrane includes a second irrigation aperture aligned with the first irrigation aperture.

10. The electrophysiology catheter of claim 9, in which the contact electrode includes a first exclusion zone surrounding the first irrigation aperture.

11. The electrophysiology catheter of claim 10, in which the wiring electrode includes a second exclusion zone surrounding the first irrigation aperture.

12. The electrophysiology catheter of claim 8, in which the wiring electrode comprises an elongated body longitudinally aligned with the elongated portion.

13. The electrophysiology catheter of claim 12, in which the wiring electrode includes a solder pad.

14. The electrophysiology catheter of claim 13, in which the flex circuit electrode assembly includes a wire pair connected to the solder pad.

15. The electrophysiology catheter of claim 14, in which the flex circuit electrode assembly further includes:

a contact microelectrode;

a wiring microelectrode; and a second conductive via connecting the contact microelectrode and the wiring electrode.

16. The electrophysiology catheter of claim 15, in which the solder pad is located remotely from the contact microelectrode.

17. The electrophysiology catheter of claim 16, in which the flex circuit electrode assembly further includes an exclusion zone about the contact microelectrode.

18. The electrophysiology catheter of claim 16, in which the flex circuit electrode assembly further includes an exclusion zone about the wiring microelectrode.

19. The electrophysiology catheter of claim 15, in which the wire pair comprises a copper conductor connected to a constantan conductor by a third conductive via.

20. The electrophysiology catheter of claim 19, in which the wire pair is formed as conducting lines in the substrate.

21. The electrophysiology catheter of claim 20, in which the third conductive via is further connected to the contact microelectrode.

22. The electrophysiology catheter of claim 8, in which the plurality of radiating strips comprises ten radiating strips.

23. The electrophysiology catheter of claim 8, in which the contact electrode has a length of between about 0.1 inches and about 1.0 inches.

24. The electrophysiology catheter of claim 23, in which the length of the contact electrode is between about 0.5 inches and about 0.7 inches.

25. The electrophysiology catheter of claim 24, in which the length of the contact electrode is about 0.57 inches.

26. The electrophysiology catheter of claim 8, in which the wiring electrode comprises a distal portion split from a proximal portion.

27. The electrophysiology catheter of claim 26, in which the distal portion of the wiring electrode comprises a radiopaque marker.

28. The electrophysiology catheter of claim 27, in which the radiopaque marker comprises an enlarged portion on a lateral side thereof.

29. The electrophysiology catheter of claim 28, in which the contact electrode comprises a distal portion split from a proximal portion.

\* \* \* \* \*